US009024507B2

(12) United States Patent
Lewis et al.

(10) Patent No.: US 9,024,507 B2
(45) Date of Patent: May 5, 2015

(54) ULTRASOUND WAVE GENERATING APPARATUS

(75) Inventors: George K. Lewis, Ithaca, NY (US); William Olbricht, Ithaca, NY (US)

(73) Assignee: Cornell University, Ithaca, NY (US)

( * ) Notice: Subject to any disclaimer, the term of this patent is extended or adjusted under 35 U.S.C. 154(b) by 83 days.

(21) Appl. No.: 13/003,201

(22) PCT Filed: Jul. 10, 2009

(86) PCT No.: PCT/US2009/050297
§ 371 (c)(1), (2), (4) Date: Feb. 24, 2011

(87) PCT Pub. No.: WO2010/006293
PCT Pub. Date: Jan. 14, 2010

(65) Prior Publication Data
US 2011/0285244 A1    Nov. 24, 2011

Related U.S. Application Data

(60) Provisional application No. 61/079,712, filed on Jul. 10, 2008.

(51) Int. Cl.
*B06B 1/02* (2006.01)
*A61N 7/02* (2006.01)

(52) U.S. Cl.
CPC .. *A61N 7/02* (2013.01); *B06B 1/023* (2013.01)

(58) Field of Classification Search
CPC .... B06B 1/023; B06B 1/0603; B06B 1/0644; B06B 1/0662
USPC .................................. 310/317, 322, 334, 335
See application file for complete search history.

(56) References Cited

U.S. PATENT DOCUMENTS 3,912,981 A  10/1975  Tsurushima
3,921,089 A  11/1975  Tsurushima
(Continued)

FOREIGN PATENT DOCUMENTS

CN  1078666   11/1993
CN  1586672   3/2005
(Continued)

OTHER PUBLICATIONS

International Rectifier IRL2910 datasheet, May 1998.*
(Continued)

*Primary Examiner* — Derek Rosenau
(74) *Attorney, Agent, or Firm* — Heslin Rothenberg Farley & Mesiti P.C.; George S. Blasiak, Esq.

(57) ABSTRACT

In one embodiment, there is provided in an ultrasound wave generating apparatus a low output impedance transistor based driver circuit that has the ability to apply a drive signal at a frequency corresponding to an ultrasound transducer's resonant frequency. The low output impedance of the driver circuit allows for a substantial portion of the energy to be delivered to the ultrasound transducer and converted to ultrasound energy. The power transfer efficiency of the presented circuit allows ultrasound drivers to be powered by portable battery packs, while still delivering high ultrasound acoustic power. The ultrasound driver can provide energy in sufficient amounts making it suitable for a range of ultrasound driving application including but not limited to therapeutic low and high power clinical systems, high intensity focused ultrasound HIFU, acoustical welding, industrial inspection, and other various forms of low-to-high power acoustic devices.

78 Claims, 21 Drawing Sheets

(56) References Cited

U.S. PATENT DOCUMENTS

| | | | |
|---|---|---|---|
| 4,128,813 A | 12/1978 | Suzuki et al. | |
| 4,246,792 A | 1/1981 | Matzuk | |
| 4,511,815 A | 4/1985 | Wood | |
| 4,532,443 A | 7/1985 | Glennon | |
| 4,685,925 A * | 8/1987 | Childress et al. | 623/25 |
| 4,733,194 A | 3/1988 | Roehrs et al. | |
| 4,827,223 A | 5/1989 | Gross | |
| 4,890,580 A | 1/1990 | Owen et al. | |
| 4,958,327 A | 9/1990 | Saitoh et al. | |
| 4,961,100 A * | 10/1990 | Baliga et al. | 257/172 |
| 5,199,299 A | 4/1993 | Hughes et al. | |
| 5,316,000 A * | 5/1994 | Chapelon et al. | 310/334 |
| 5,425,704 A | 6/1995 | Sakurai et al. | |
| 5,633,801 A | 5/1997 | Bottman | |
| 5,957,846 A | 9/1999 | Chiang et al. | |
| 5,957,851 A | 9/1999 | Hossack | |
| 5,964,709 A | 10/1999 | Chiang et al. | |
| 5,995,348 A | 11/1999 | McCartan et al. | |
| 6,008,550 A * | 12/1999 | Dorsey et al. | 307/141 |
| 6,114,898 A | 9/2000 | Okayasu | |
| 6,126,608 A | 10/2000 | Kemme et al. | |
| 6,169,709 B1 * | 1/2001 | Schafroth | 368/203 |
| 6,212,426 B1 | 4/2001 | Swanson | |
| 6,320,239 B1 | 11/2001 | Eccardt et al. | |
| 6,380,766 B2 | 4/2002 | Savord | |
| 6,414,549 B1 | 7/2002 | Barbetta | |
| 6,416,478 B1 | 7/2002 | Hossack | |
| 6,471,651 B1 | 10/2002 | Hwang et al. | |
| 6,540,685 B1 | 4/2003 | Rhoads et al. | |
| 6,542,846 B1 | 4/2003 | Miller et al. | |
| 6,569,102 B2 | 5/2003 | Imran et al. | |
| 6,579,244 B2 | 6/2003 | Goodwin | |
| 6,592,521 B1 | 7/2003 | Urbano et al. | |
| 6,806,623 B2 * | 10/2004 | Petersen et al. | 310/334 |
| 6,856,175 B2 | 2/2005 | Wodnicki | |
| 6,875,178 B2 | 4/2005 | Phelps et al. | |
| 6,994,674 B2 | 2/2006 | Sheljaskow et al. | |
| 7,307,373 B2 * | 12/2007 | Straub et al. | 310/334 |
| 7,314,445 B2 | 1/2008 | Wodnicki et al. | |
| 7,336,019 B1 | 2/2008 | Puskas | |
| 7,500,952 B1 | 3/2009 | Chiang et al. | |
| 7,777,394 B2 * | 8/2010 | Amemiya | 310/316.03 |
| 7,828,736 B2 * | 11/2010 | Tanaka | 600/459 |
| 2002/0181251 A1 * | 12/2002 | Kompelien | 363/17 |
| 2003/0039173 A1 | 2/2003 | Yurchenko et al. | |
| 2003/0139664 A1 | 7/2003 | Hunt et al. | |
| 2004/0138569 A1 | 7/2004 | Grunwald et al. | |
| 2004/0158154 A1 | 8/2004 | Hanafy et al. | |
| 2005/0113698 A1 | 5/2005 | Kristoffersen et al. | |
| 2005/0154300 A1 * | 7/2005 | Wodnicki et al. | 600/437 |
| 2006/0217602 A1 | 9/2006 | Abul-Haj et al. | |
| 2007/0027508 A1 | 2/2007 | Cowan | |
| 2007/0157404 A1 | 7/2007 | Brewer et al. | |
| 2007/0159422 A1 * | 7/2007 | Blandino et al. | 345/82 |
| 2007/0232910 A1 | 10/2007 | Hwang et al. | |
| 2008/0021327 A1 | 1/2008 | El-Bialy et al. | |
| 2008/0146922 A1 | 6/2008 | Steins et al. | |
| 2008/0300490 A1 | 12/2008 | Chiang et al. | |
| 2009/0015096 A1 | 1/2009 | Puskas | |
| 2009/0043203 A1 | 2/2009 | Pelissier et al. | |
| 2009/0062652 A1 | 3/2009 | Shin et al. | |
| 2009/0112091 A1 | 4/2009 | Chiang et al. | |
| 2011/0051476 A1 * | 3/2011 | Manor et al. | 363/65 |
| 2011/0234157 A1 * | 9/2011 | Knight | 320/108 |

FOREIGN PATENT DOCUMENTS

| | | |
|---|---|---|
| CN | 1603065 | 4/2005 |
| CN | 101144798 A | 3/2008 |
| WO | WO-2010006293 A9 | 1/2010 |

OTHER PUBLICATIONS

Patent Cooperation Treaty International Bureau, Notification Concerning Transmittal of Copy of International Preliminary Report on Patentability, International Application No. PCT/US2009/050297, dated Jan. 20, 2011 (1 page).

Patent Cooperation Treaty, International Preliminary Report on Patentability, International Application No. PCT/US2009/050297, dated Jan. 11, 2011 (1 page).

Patent Cooperation Treaty, Written Opinion of the International Searching Authority, International Application No. PCT/US2009/050297, dated Mar. 10, 2010 (4 pages).

International Search Report, International Application No. PCT/US2009/050297, dated Mar. 10, 2010 (7 pages).

C. M. H. Newman and T. Bettinger "Gene therapy progress and prospects: Ultrasound for gene transfer" Gene Therapy, vol. 14, pp. 465-475, 2007.

D. Cesario and et al. "Selection of Ablation Catheters, Energy Sources, and Power Delivery" Contemporary Cardiology, Atrial Fibrillation, pp. 209-221, ISBN: 978-1-58829-856-0 (Print) 978-1-59745-163-5 (Online), 2008.

E. J. Park, K. I. Jung, and S. W. Yoon "Acoustic mechanisms as an enhancer for transdermal drug delivery" J. Acoustical Society of America, vol. 107, pp. 2788, 2005.

European Association of Urology, G. Aus, "Current Status of HIFU and Cryotherapy in Prostate Cancer—A Review," vol. 50 pp. 927-934, dated Jul. 11, 2006 (8 pages).

European Patent Office, Entry into the European phase before the European Patent Office and International Search Report, European Patent Application No. 09795258.4 PCT/US2009050297, dated Nov. 19, 2010, (10 pages).

F. L. Lizzi, D. J. Driller, R. H. Silverman, B. Lucas, and A. Rosado, "A therapeutic ultrasound"—S. Vaezy, X, Shi, R. W. Martin, E. Chi, P. I. Nelson, M. R. Bailey, and L. A. Crum, "Real-time visualization of high-intensity focused ultrasound treatment using ultrasound imaging," *Ultrasonics Symposium*, pp. 981-979, 1986. En.

G. K. Lewis, Jr., W. Olbricht, and G. K. Lewis "Acoustic enhanced Evans blue dye perfusion in neurological tissues" Acoustical Society of America, POMA, vol. 2, 2008.

G. ter Harr and C. Coussios "High Intensity focused ultrasound: Physical principles and devices" International Journal of Hyperthermia, vol. 23, pp. 89-104, 2007.

Intersil, Ultra-High Current Pin Driver, Reference No. EL7158, dated May 14, 2007, (9 pages).

J. Wu and W. L. M. Nyborg, "Emerging Therapeutic Ultrasound" Ultrasonics in Medicine, ISBN 978-981-256-685-0 (Print), 2006.

L. A. Crum "Smart Therapeutic Ultrasound Device for Mission-Critical Medical Care" Project Report, NASA, 2007.

M. R. Bailey, V. A. Khokhlova, O. A. Sapozhnikov, S. G. Kargl, and L. A. Crum, "Physical mechanisms of the therapeutic effect of ultrasound: (A review)," *Acoust. Phys.*, vol. 49, No. 4, pp. 369-388, 2003.

N.I. Vykhodtseva, K. Hynynen, C. Damianou, "Histologic effects of high intensity pulsed ultrasound exposure with subharmonic emission in rabbit brain in vivo", Ultrasound Med. Blol. vol. 21, pp. 969-979, 1995.

National Institute of Health Author Manuscript, Lewis, George K. and Olbricht, William, "Development of a Portable Therapeutic and High Intensity Ultrasound System for Military, Medical and Research Use," doi: 10.1063/1.3020704, dated Nov. 2008 (14 pages).

Nature Reviews Drug Discovery, S. Mitragotri, "Healing Sound: The Use of Ultrasound in Drug Delivery and Other Therapeutic Applications," vol. 4, pp. 255-260, dated 2005 (6 pages).

Review of Scientific Instruments, Lewis, George K. and Olbricht, William L., "Development of a Portable Therapeutic and High Intensity Ultrasound System for Military, Medical, and Research Use," dated Nov. 11, 2008 (7 pages).

S. Maruvada, G. R. Harris, and B. A. Herman "Acoustic power calibration of high-intensity focused ultrasound transducers using a radiation force technique" J. Acoustical Society of America, vol. 121, pp. 1434-1439, 2007.

S. Vaezy, X, Shi, R. W. Martin, E. Chi, P. I. Nelson, M. R. Bailey, and L. A. Crum, "Real-time visualization of high-intensity focused ultrasound treatment using ultrasound imaging," Ultrasound Med. Blol., vol. 27, pp. 33-42, 2001.

(56) References Cited

OTHER PUBLICATIONS

Texas Instruments, CMOS Dual Complementary Pair Plus Inverter, Reference No. CD4007UP Types, Revised Sep. 2003, (14 pages).
University of Michigan, Maharbiz, Lecture 5: CMOS Inverter, Fall 2007 (29 pages).
May 30, 2013 Office Action in Chinese Application No. 200980135529.1, 6 pages (with English translation).
Apr. 23, 2014 Office Action in Chinese Application No. 200980135529.1, 18 pages (Cited with copy of original Chinese language document and with English translation).
Owen et al., Development of Power Supplies for Portable HIFU Therapy Systems, in Int. Symp. on Therapeutic Ultrasound, pp. 399-404. 2003.
Redwood et al., On the Measurement of Attenuation in Ultrasonic Delay Lines, Proceedings of the IEEE, vol. 103, pp. 773-780, 1956.
International Rectifier, PD-94336B, IRF7350, HEXFET Power MOSFET, www.irf.com Aug. 9, 2001.
Fairchild Semiconductor, 60V Complementary PowerTrench MOSFET. FDS4559 Rev. C1(W), Apr. 2002.
Jan. 12, 2015 Office Action for corresponding Chinese Patent Application No. 200980135529.1 (with English Translation).

* cited by examiner

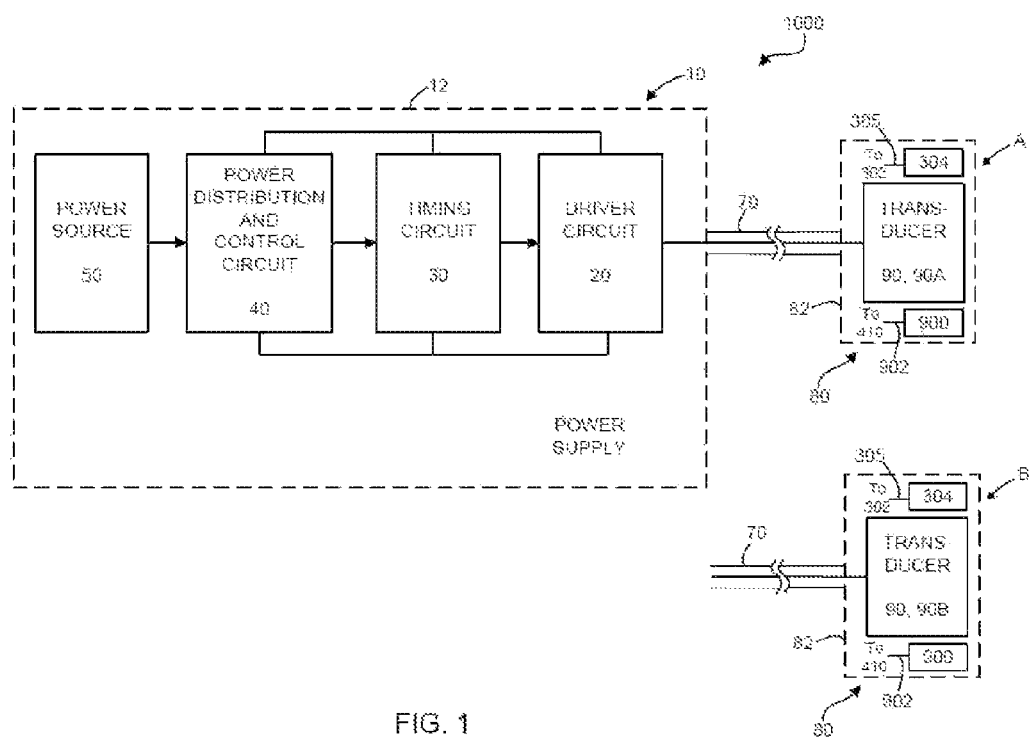
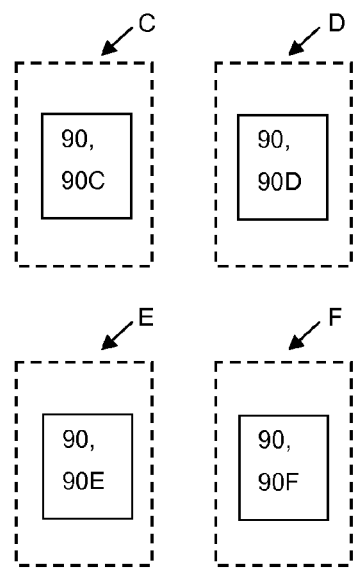
FIG. 1

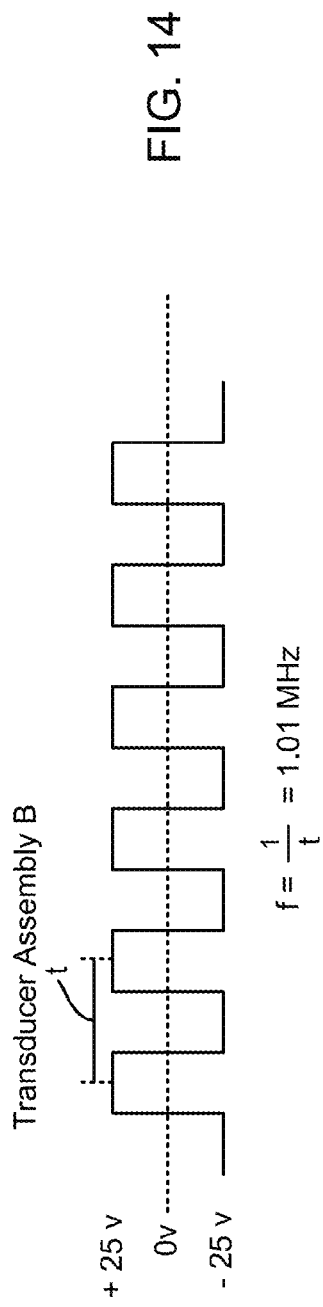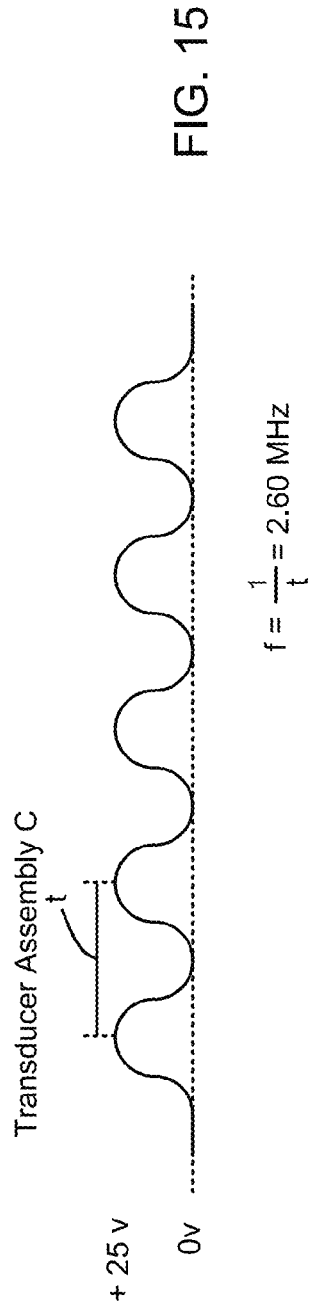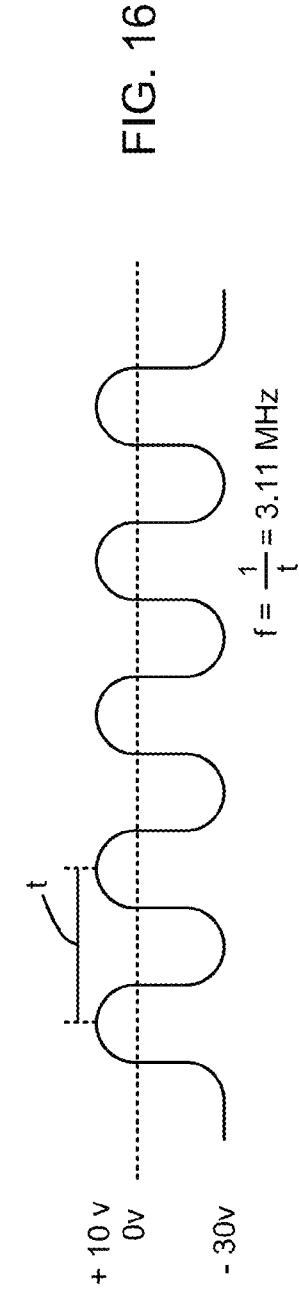

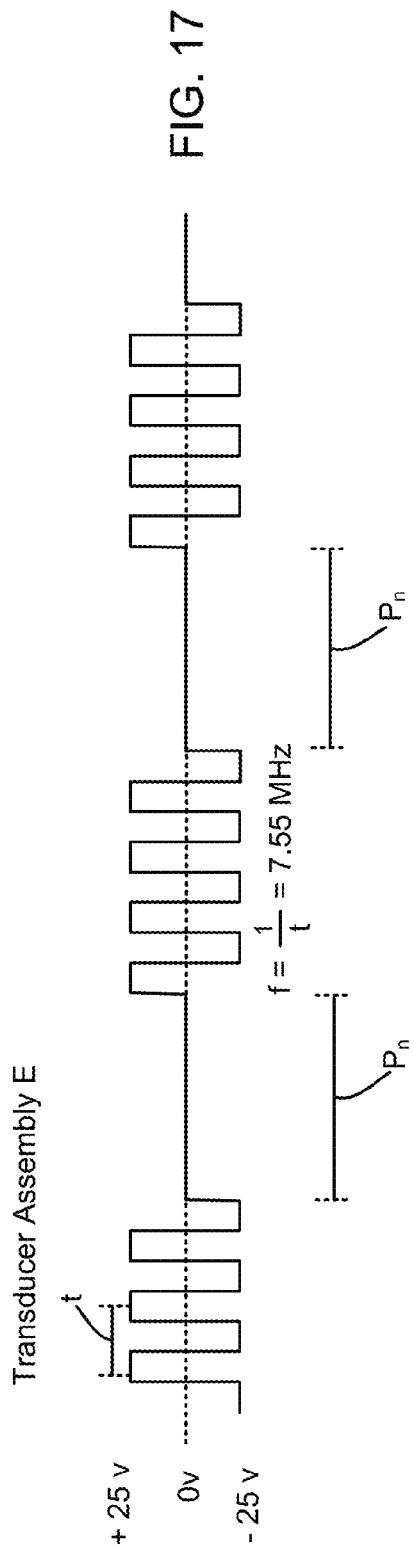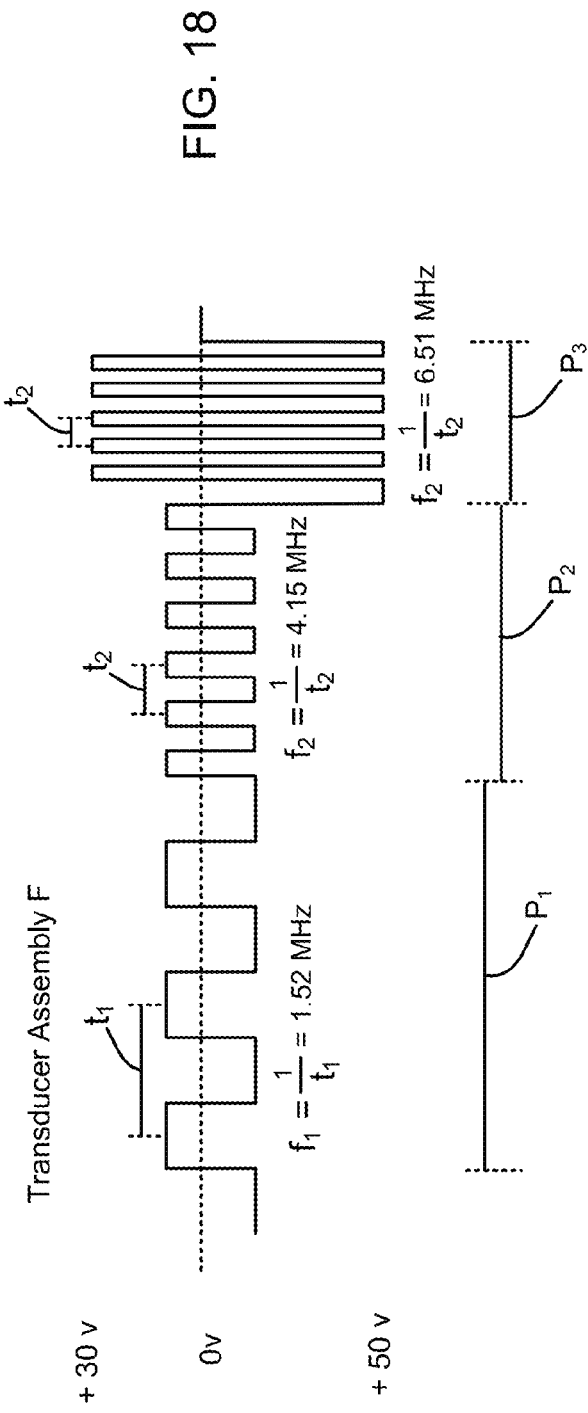

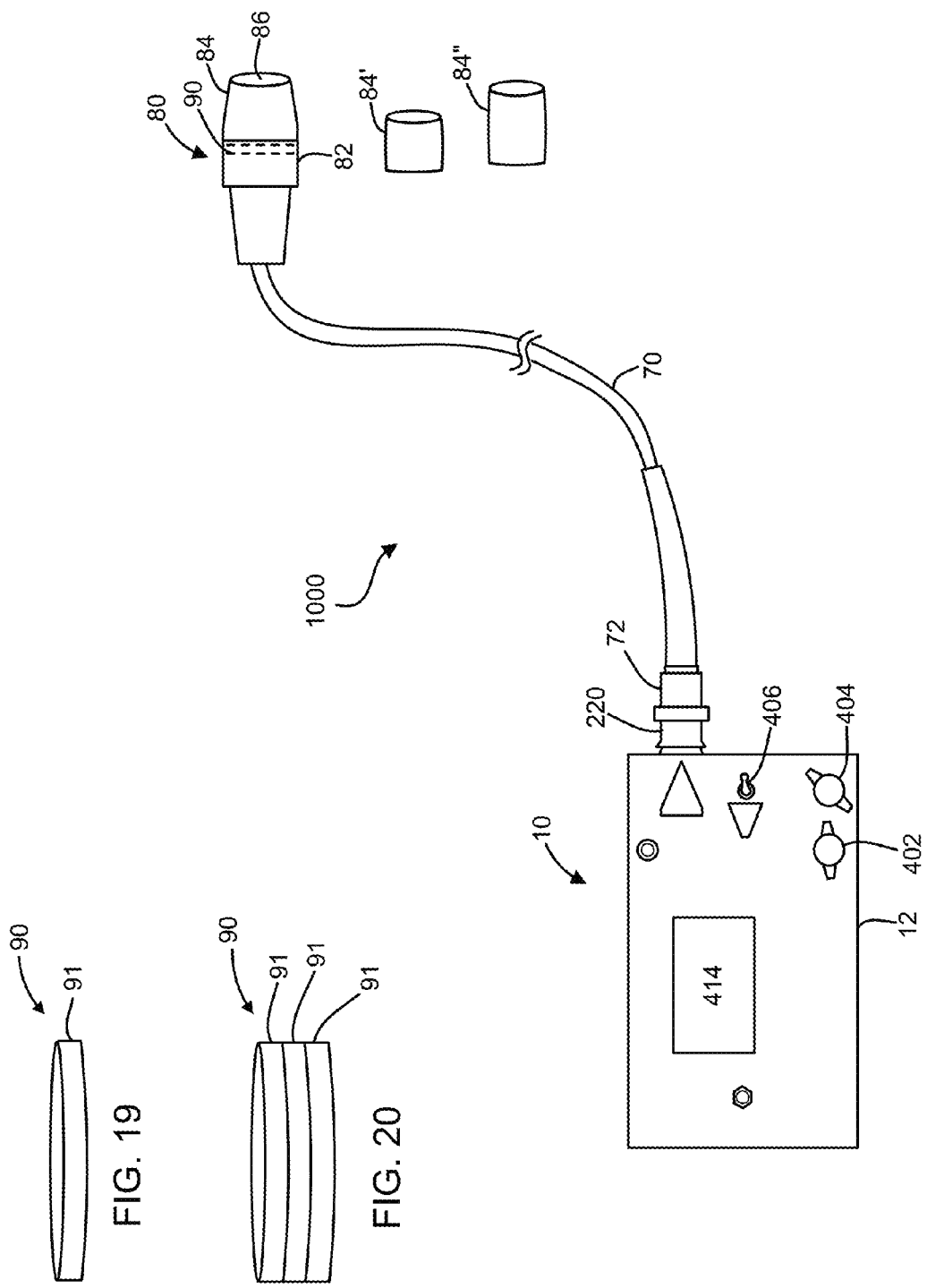

ULTRASOUND WAVE GENERATING APPARATUS

CROSS REFERENCE TO RELATED APPLICATIONS

This application is a National Stage application under 35 U.S.C. §371 of PCT Application No. PCT/US2009/050297, filed Jul. 10, 2009, entitled "Ultrasound Wave Generating Apparatus," which claims priority to U.S. Application No. 61/079,712, filed Jul. 10, 2008, entitled "Portable Low Output Impedance Ultrasound Transducer Driver," which is incorporated herein by reference.

STATEMENT REGARDING FEDERALLY SPONSORED RESEARCH OR DEVELOPMENT

This invention was made with Government support under a grant/contract awarded by the National Institutes of Health under grant/contract No.: NS045236. The United States Government has certain rights in the invention.

FIELD OF THE INVENTION

This invention relates to transducer provisioned apparatuses in general and in particular to ultrasound wave generating apparatuses for use in a wide variety of applications.

BACKGROUND OF THE INVENTION

In the last two decades therapeutic ultrasound has received attention from the medical community as a tool to relieve arthritis, to improve rehabilitation, and to enhance wound healing processes. Ultrasound at higher energies plays a role in surgical applications such as prostate therapy, and brain tumor and cardiac tissue ablation. Therapeutic ultrasound and its effects on tissue properties are currently being studied in research. For example, researchers are assessing the ability of ultrasound for large molecule transdermal drug delivery, in targeted chemotherapy delivery to brain cancer, and in cellular gene transfer applications. The potential of a combined portable ultrasound imaging and therapeutic system is currently being studied to great lengths for military, industrial, and medical applications. Despite the widespread use of ultrasound, the basic hardware has not changed significantly in the past 50 years.

The ability to drive ultrasound transducers for therapeutic, surgical, mechanical, military, and other applications is of importance to medical doctors and acoustical engineers and professionals in numerous additional fields.

SUMMARY OF THE INVENTION

In one embodiment, there is provided an ultrasound wave generating apparatus having a low output impedance transistor based driver circuit that has the ability to apply a drive signal at a frequency corresponding to an ultrasound transducer's resonant frequency. The low output impedance of the driver circuit allows for a substantial portion of the energy to be delivered to the ultrasound transducer and converted to ultrasound energy. The power transfer efficiency of the presented circuit allows ultrasound drivers to be powered by portable battery packs, while still delivering high ultrasound acoustic power. The ultrasound driver can provide energy in sufficient amounts making it suitable for a range of ultrasound driving applications including but not limited to therapeutic low and high power clinical systems, high intensity focused ultrasound HIFU, acoustical welding, industrial inspection, and other various forms of low-to-high power acoustic devices. Other embodiments of ultrasound transducer drivers and of other components of portable ultrasound generator apparatus in various embodiments are set forth herein.

In another embodiment, a low output impedance power supply can be incorporated in a portable ultrasound sensing apparatus. Various embodiments of an ultrasound sensing apparatus are set forth herein.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 1 is a schematic block diagram of an ultrasound wave generating apparatus;

FIGS. 13-18 are signal plots illustrating specific output drive signals, each being associated with a particular candidate transducer assembly of a set of candidate transducer assemblies;

FIG. 19 is a diagram showing a single transducer element ultrasound transducer;

FIG. 20 is a diagram showing a plural transducer element ultrasound transducer;

FIG. 21 is a physical form view of an ultrasound wave generating apparatus in one embodiment;

DETAILED DESCRIPTION OF THE INVENTION

Figure 2:
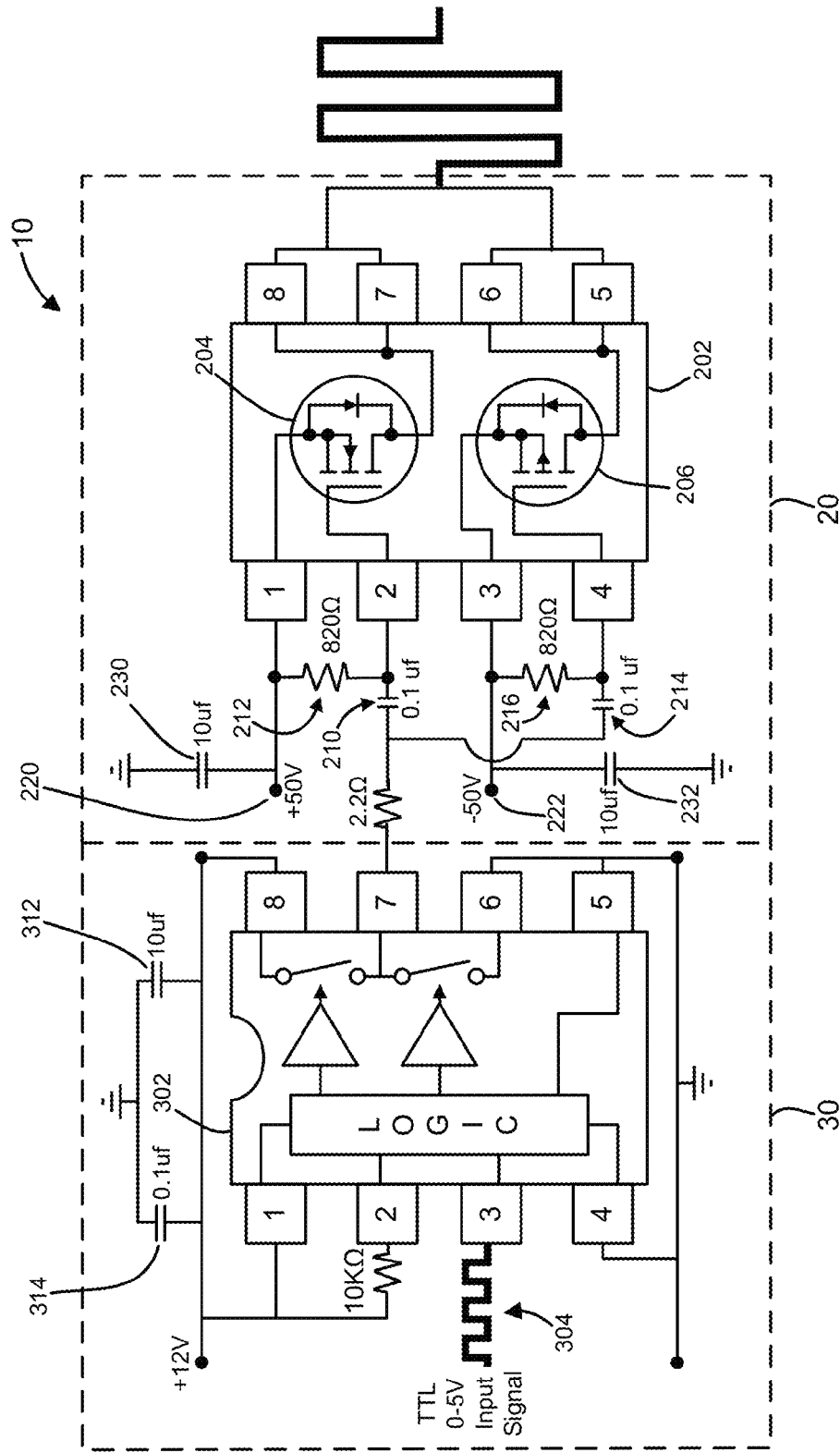
FIG. 2 is a schematic diagram of a driver circuit in combination with a timing circuit.

A high level schematic diagram of an ultrasound wave generating apparatus is shown and described with reference to FIG. 1. Ultrasound wave generating apparatus 1000 can include a power supply 10, and an ultrasound probe 80 having a transducer 90 operative for emission of ultrasound waves. Ultrasound probe 80 can emit waves at a frequency within the ultrasound frequency range of from about 20 kHz to about 200 MHz. In some embodiments, ultrasound wave generating apparatus 1000 can also include a transmission line 70.

Referring to power supply 10, power supply 10 can include driver circuit 20, timing circuit 30, power distribution and control circuit 40, and power source 50. Driver circuit 20 can be operative to have low output impedance, e.g. of under 0.5 Ohms. Power supply 10 can be housed in a housing 12 as is represented by dashed in border 12. Power supply 10 and its associated housing 12 in one embodiment can be portable and in one embodiment power supply 10 and housing 12 can be hand held. Probe 80 can include an ultrasound transducer 90 which emits ultrasound waves in response to electrical signals received thereby. Transducer 90 can be housed in a probe housing 82 as is represented by dashed in border 82. Probe 80 and its associated housing 82 in one embodiment can be portable and in one embodiment probe 80 and associated housing 82 can be hand held.

In one embodiment, transmission line 70 can be deleted and ultrasound wave generating apparatus 1000 can include a single housing. For example, transducer 90 can be housed in housing 12, or power supply 10 can be housed in housing 82 of probe 80.

Ultrasound wave generating apparatus 1000 can be configured to be operative in a single, or alternatively in multiple operating modes. A drive signal output by power supply 10 can have a different set of characteristics for each operating mode. Further, ultrasound wave generating apparatus 1000 can be operative so that an operating mode of apparatus 1000 and therefore output drive signal changes in response to control inputs that are input into apparatus 1000 by an operator. In some possible operating modes, power supply 10 outputs a continuous drive signal at a steady state frequency. A mode of operation where power supply 10 outputs a continuous drive signal is useful, in a wide range of applications e.g., in ultrasound therapy medical applications, imaging applications, industrial applications, automobile applications, fuel cell applications, water purification applications, filtering applications, food industry applications, industrial applications, ultrasound therapy medical applications, commercial cutting applications, small particle removal applications, industrial and/or commercial mixing applications, and liquid vaporization applications. In another mode of operation, power supply 10 is operative to output a short burst drive signal. Such mode is useful in a wide range of applications, e.g., in ultrasound therapy medical applications, imaging applications, and industrial applications. The emission of ultrasound waves by apparatus 1000 either in a continuous mode or a burst mode can also be useful, e.g., for cooling of electric motors by recycling bubbles in a coolant, aiding in cooling of batteries, preparation of substrates for fermentation, assisting in distillation of mixed bio-fuels and waste, assisting the converting of plant oils to biodiesel by cavitation, desalinating and purifying water, and preparing of crude oils.

Driver circuit 20 in one embodiment can include a transistor pair having associated first and second clamping voltage terminals, where the clamping voltage terminals have voltages that are alternately passed to an output of the driver circuit. The transistor pair can be controlled with an oscillating timing signal for controlling timing of the switching of the transistors of the transistor pair so that the transistors of the transistor pair alternate between conducting and non-conducting states. With the transistors of the transistor pair alternating between conducting and non-conducting states, the voltages of the first and second clamping voltage terminals can be alternately applied to the output of the driver circuit. The driver circuit can be provisioned to include a low output impedance that is mismatched with respect to the impedance of the transducer. The provisioning of the driver circuit to include a low output impedance provides numerous advantages as will be set forth further herein.

In one embodiment, a plurality of the described transistor pairs can be connected in parallel for reduction of an output impedance of the driver circuit, and for increasing an output current capacity of the driver circuit. The driver circuit can be configured to have an output current capacity of more than 50 Amperes while being capable of outputting an output drive signal of relatively low voltage. Outputting an output signal of low voltage, e.g., 50V or lower is advantageous in a variety of applications where a higher output voltage can pose a risk to humans.

In another aspect, the output drive signal output by the driver circuit for driving the ultrasound transducer can be a bipolar signal having alternatingly positive and negative polarities. Configuring a driver circuit to output a bipolar drive signal provides variation in the forces imparted to transducer 90 for causing vibration thereof, thus increasing an expected lifetime and performance of transducer 90. In another aspect, an applied bipolar drive signal can be an imbalanced bipolar signal so that compression forces are imparted to transducer in greater magnitudes than expansion forces.

In one embodiment, ultrasound wave generating apparatus 1000 is configured to be a single mode apparatus so that at all times, when operative to output a drive signal, the ultrasound wave generating apparatus 1000 outputs a drive signal having the same set of characteristics. However, in one embodiment, the ultrasound wave generating apparatus 1000 can include enhanced control features configuring the ultrasound wave generating apparatus so that an operator, e.g., via actuation of control actuator of a user interface of the apparatus, can adjust one or more characteristics of an output drive signal to change a mode of operation of the apparatus. Drive signal characteristics that can be subject to adjustment can include such characteristics as amplitude, frequency, maximum positive voltage, minimum negative voltage, and the pattern (e.g., "continuous pattern," "burst pattern") of the apparatus's output drive signal. Apparatus 1000 can be operative so that an operator can adjust one or more characteristics of a drive signal via actuation of a user interface actuator. Apparatus 1000 can also be operative so that an operator can adjust one or more characteristics of a drive signal via replacement of a transducer assembly, as is set forth herein.

In one embodiment, ultrasound wave generating apparatus 1000 can be provisioned so that a transducer assembly of apparatus 1000 is replaceable and further so that differently configured candidate transducer assemblies can be associated to power supply 10. In one example, each of plurality of candidate transducer assemblies can include a probe 80 and a transmission line 70 terminating in a detachable connector 72 that can be detachably coupled with a connector 220 (see FIG. 21) of power supply 10. The ultrasound wave generating apparatus 1000 can be configured so that each candidate transducer assembly that can be associated to power supply 10 has an associated output drive signal having a predetermined set of characteristics well suited for driving the transducer of the particular associated transducer assembly. The ultrasound wave generating apparatus 1000 can be configured so that the specific output drive signal output by driver circuit 20 is responsive to which of a plurality of transducer assemblies is presently attached to the power supply 10. In one embodiment, apparatus 1000 can be configured so that an output drive signal that is specific to a particular transducer assembly can be subject to adjustment via control inputs that are input to apparatus 1000 by an operator using a user interface of apparatus 1000.

Referring now to FIG. 2, a schematic diagram of driver circuit 20 in combination with timing circuit 30 in a particular embodiment is shown and described. In general, in one embodiment, an output of driver circuit 20 can be responsive to a timing signal output by timing circuit 30 which controls a timing of an output drive signal. As shown in FIG. 2, driver circuit 20 can include at least one transistor pair 204 and 206 having associated first and second clamping voltage terminals. A timing signal output by timing circuit 30 can be operative to cause switching between transistors of the transistor pair for output of a signal that varies between output of the voltage at the first clamping voltage terminal and the voltage at the second clamping voltage terminal. In the embodiment of FIG. 2, driver circuit 20 is provided by a transistor push pull pair having first and second clamping terminal voltages. In the embodiment described, the first clamping voltage terminal 220 can be clamped to +50V and the second clamping voltage terminal 222 can be clamped to −50V. Referring to timing circuit 30, an oscillating timing signal can be output by timing circuit 30 for causing alternating switching of transistor 204 and transistor 206. In the embodiment of FIG. 2, transistor 204 and 206 are provided by metal oxide semiconductors field effect transducers (MOSFETs). First transistor 204 clamped to the first clamping voltage terminal (+50V) is provided by a PMOS transistor, while the second clamping voltage terminal (−50V) is provided by an NMOS transistor. Timing circuit 30 in the particular embodiment of FIG. 2 includes a pin driver integrated circuit 302 that outputs at pin 7 thereof a unipolar 0V-12V timing signal. In another embodiment, transistors 204 and 206 can be provided by bipolar junction transistors (BJTs). Driver circuit 20 in the embodiments set forth herein can have inactive and active states. An active state of driver circuit 20 is defined when there is a time varying voltage present at the output of the driver circuit 20.

In the particular embodiment as shown in FIG. 2, a transistor pair 204, 206 of driver circuit 20 can include a plurality of Metal Oxide Semiconductor Field Effect Transistors (MOSFETs) arranged in a particular configuration. In the embodiment of FIG. 2, a pair of MOSFETs namely, PMOS transistor 204 and NMOS transistor 206 are provided on a common integrated circuit 202 and are arranged in a push pull configuration. In the particular embodiment, a timing signal output of timing circuit 30 is commonly applied as a gate drive signal to the gates of transistors 204 and 206 through a capacitive coupling circuit. Further regarding MOSFET push pull pair 204 and 206, an oscillating timing signal having a timing controlled by the output of the timing circuit 30 can be commonly applied to gates of the respective push pull pair and respective sources of the pair can be clamped to first and second respective terminal voltages. With the noted oscillating timing signal applied to the MOSFET pair, (PMOS and NMOS) the pair can oscillate between a first state in which PMOS transistor 204 conducts and NMOS transistor 206 is cut off and a second state in which NMOS transistor 206 conducts and PMOS transistor 204 is cut off.

Figure 10:
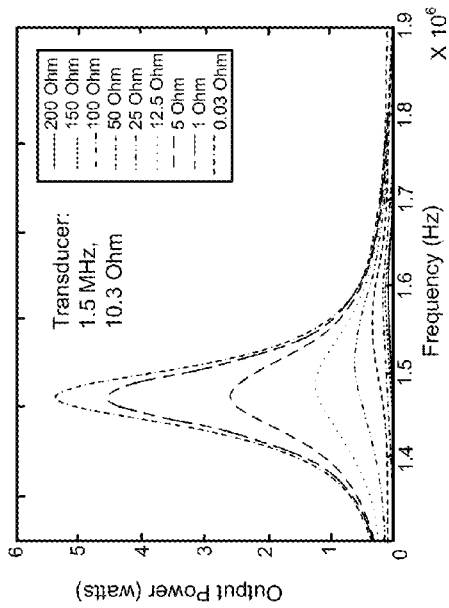
FIG. 10 is a Mason model power output chart for an ultrasound transducer in one embodiment; where the ultrasound transducer is provided by a 10.6 Ohm ultrasound transducer having a nominal frequency of resonance of 8 MHz.

With further reference to features of timing circuit 30 as shown in the embodiment of FIG. 2, pin 7 of the pin driver integrated circuit 302 in the embodiment of FIG. 2 is the output that provides a 0 to 12V square wave to regulate the switching of the MOSFET's voltage drain. As is detailed in FIG. 2, the unipolar square wave output of pin driver integrated circuit 302 can be converted into a bipolar square wave with use of capacitive coupling circuit. In the embodiment of FIG. 2, a capacitive coupling circuit is provided by coupling capacitors 210 and 214 in combination with resistors 212 and 216. From pin 7 of the pin driver 302 in the embodiment of FIG. 2, a 2.2 Ohm resistor splits off with two 0.1 µF coupling capacitors 210 and 214 into the input pins 2 and 4 of the low on resistance N/P channel MOSFET integrated circuit 202. MOSFET integrated circuit 202 can be provided by an IRF7350 MOSFET integrated circuit of the type available from International Rectifier Corporation. Further, resistor 212 is connected between pin 2 and the positive terminal voltage and resistor 216 is connected between the negative terminal voltage and pin 4 of MOSFET integrated circuit 202. Resistors 212 and 216 function to allow for a voltage differential from gate to source. MOSFET integrated circuit 202 in one embodiment can be provided by an IRF7350 MOSFET integrated circuit of the type available from International Rectifier Corporation. In another embodiment, MOSFET integrated circuit 202 can be provided by an FDS4559 integrated circuit of the type available from Fairchild Semiconductor Corporation. Pins 1 and 3 of MOSFET integrated circuit 202 are held at a maximum of −50V and +50V, respectively, with 820 Ohm resistors across pins 1-2 and 3-4. Bypass capacitors 230 and 232 are applied as well to pins 1 and 3 of the MOSFET. Capacitor 230 and capacitor 232, which, are tied to ground function to remove noise from the gate drive signal. Pins 5-6 and 7-8 of MOSFET integrated circuit 202 are tied together and coupled. The output drive signal can be applied to the ultrasound transducer through a standard BNC connector 220 as shown in FIG. 10. In one embodiment, (not shown) the pins 5-6 and 7-8 of MOSFET integrated circuit 202 can be tied together and coupled through 1 Ohm 5 W power resistors.

The use of a unipolar timing signal in combination with the capacitive coupling circuit (in the described embodiment of FIG. 2 including capacitors 210 and 214, and resistors 212 and 216), for converting the unipolar timing signal into a bipolar output for input to transistors 204 and 206 provides significant advantages. Pin driver integrated circuits of the type of pin driver integrated circuit 302 having unipolar outputs are mass produced and are available at low cost as off-the-shelf component parts. Thus, use of a unipolar timing signal allows use of a low cost component part. Further, as a unipolar output component pin driver integrated circuit 302 can be powered using a single terminal voltage, the use of a unipolar output timing circuit reduces overall power supply complexity and cost.

Referring to MOSFET integrated circuit 202, MOSFET integrated circuit 202 can include PMOS transistor 204 and NMOS transistor 206 forming a transistor pair for driver circuit 10. In the example shown, the transistors are connected in a push pull pair. An output from pin driver integrated circuit 302 as described in the embodiment of FIG. 2 can be capacitively coupled with use of a capacitive coupling circuit and input into gates of PMOS transistor 204 and NMOS transistor 206. When a square input wave 0-12V signal is capacitively coupled for output of a bipolar input signal, and where the bipolar input signal is applied to the gates of PMOS transistor 204 and NMOS transistor 206 with the source of PMOS transistor 204 clamped at a suitable clamping voltage, e.g., at +50V, and the source of NMOS transistor 206 clamped at −50V, the MOSFET pair will alternate between conditions of (a) NMOS cut off, with PMOS conducting and (b) PMOS cut off and NMOS conducting. Operating as described, a transducer driving output signal of the MOSFET pair will be a ±50V square wave. Configured as described, it will be seen that the amplitude of the output drive signal output by driver circuit 20 will be dependent essentially only on the voltages at clamping voltage terminal 220 and at clamping voltage terminal 222 but will not be dependent on an amplitude of a timing signal output by timing circuit 30. In the particular embodiment of FIG. 2, an output of timing circuit 20 can control a timing of switching of driver circuit 20; however, an amplitude of the output timing signal can have essentially no effect on an output drive signal output by driver circuit 20.

Referring to further aspects of timing circuit 30, timing circuit 30 in the embodiment of FIG. 2, pin driver integrated circuit 302 can be selected to be capable of driving high capacitive loads. Pin driver integrated circuit 302 can be provided by an EL71581SZ pin driver available from Intersil Corporation. Pin driver integrated circuit 302 can be supplied with a 5V square wave transistor-transistor logic (TTL) at pin 3. In one embodiment, the input timing signal 304 can be provided by a crystal oscillator (not shown) having an output frequency that is selected to correspond to the ultrasound probe's resonant frequency (the resonant frequency of transducer 90) for maximum power transfer. Selecting a crystal oscillator of timing circuit 30 to have an output frequency corresponding to the resonant frequency of transducer 90 provides certain advantages. An oscillator (not shown in FIG. 2) can be included by an SE1216-ND crystal oscillator integrated circuit of the type available from EPSON Toyocom Corporation. Pins 1 and 8 are held at +12V with 10 μF and bypass capacitor 312 (e.g., 10 μF, 47 μF) and bypass capacitor 314 (e.g., 0.1 μF) to ground. Pin 2 is connected to Pin 1 with a 10 k Ohm resistor. Pins 4 through 6 are connected to earth ground. Driver circuit 20 as shown in FIG. 2 has a measured low output impedance of about 0.5 Ohms when integrated circuit 202 is provided by an IRF750 integrated circuit available from International Rectifier Corporation (1.5 Ohms if 1 Ohm series power resistor is included). Where the driver circuit 20 as shown in FIG. 2 is devoid of an output series power resistor, driver circuit 20 has a current output capacity of about 10 Amperes. Schemes for decreasing an output impedance of and increasing a maximum current output capacity of driver circuit 20 are set forth herein.

Figure 3:
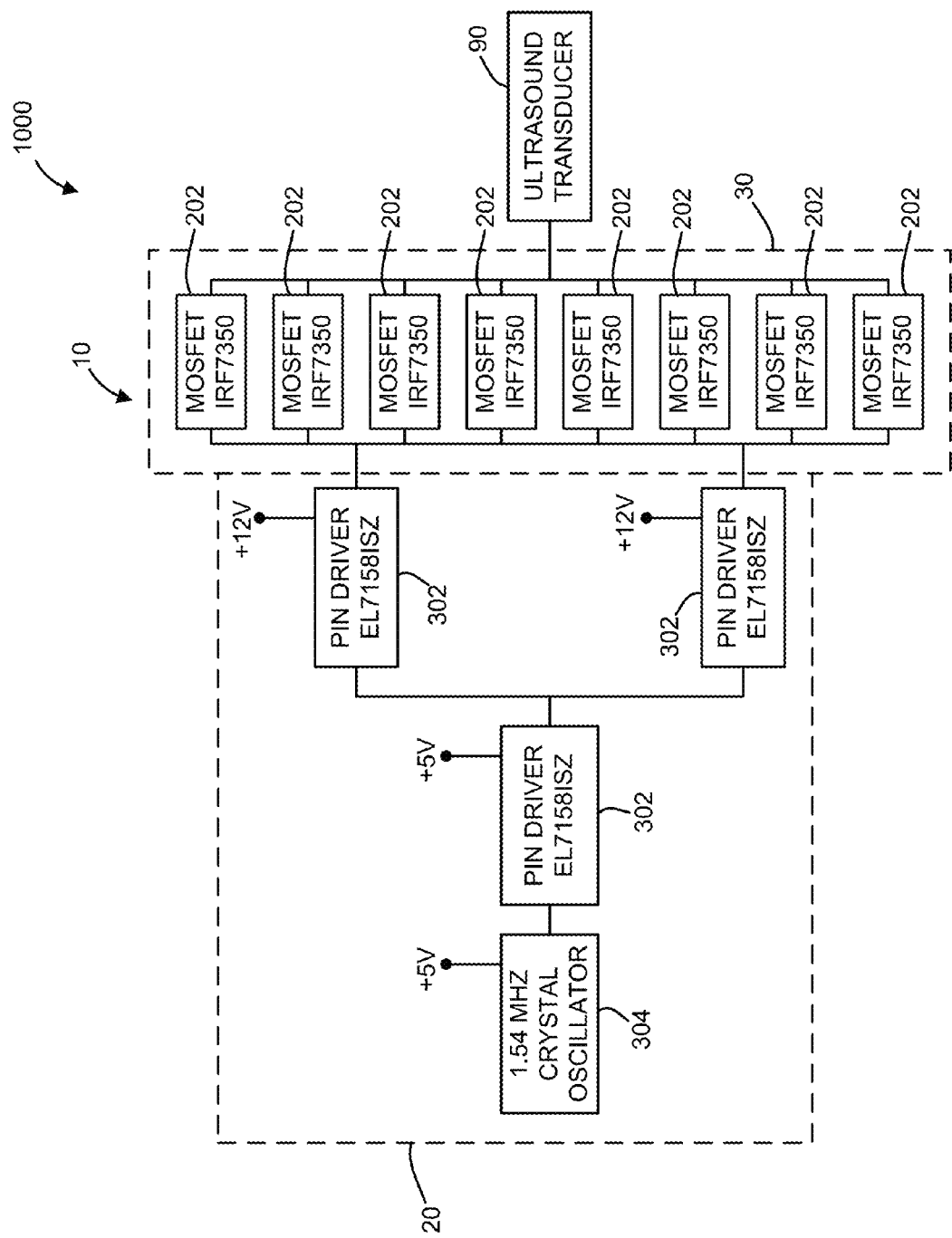
FIG. 3 is a block diagram of a driver circuit in combination with a timing circuit, wherein the driver circuit includes a plurality of transistor pairs arranged in parallel pairs.
Figure 4:
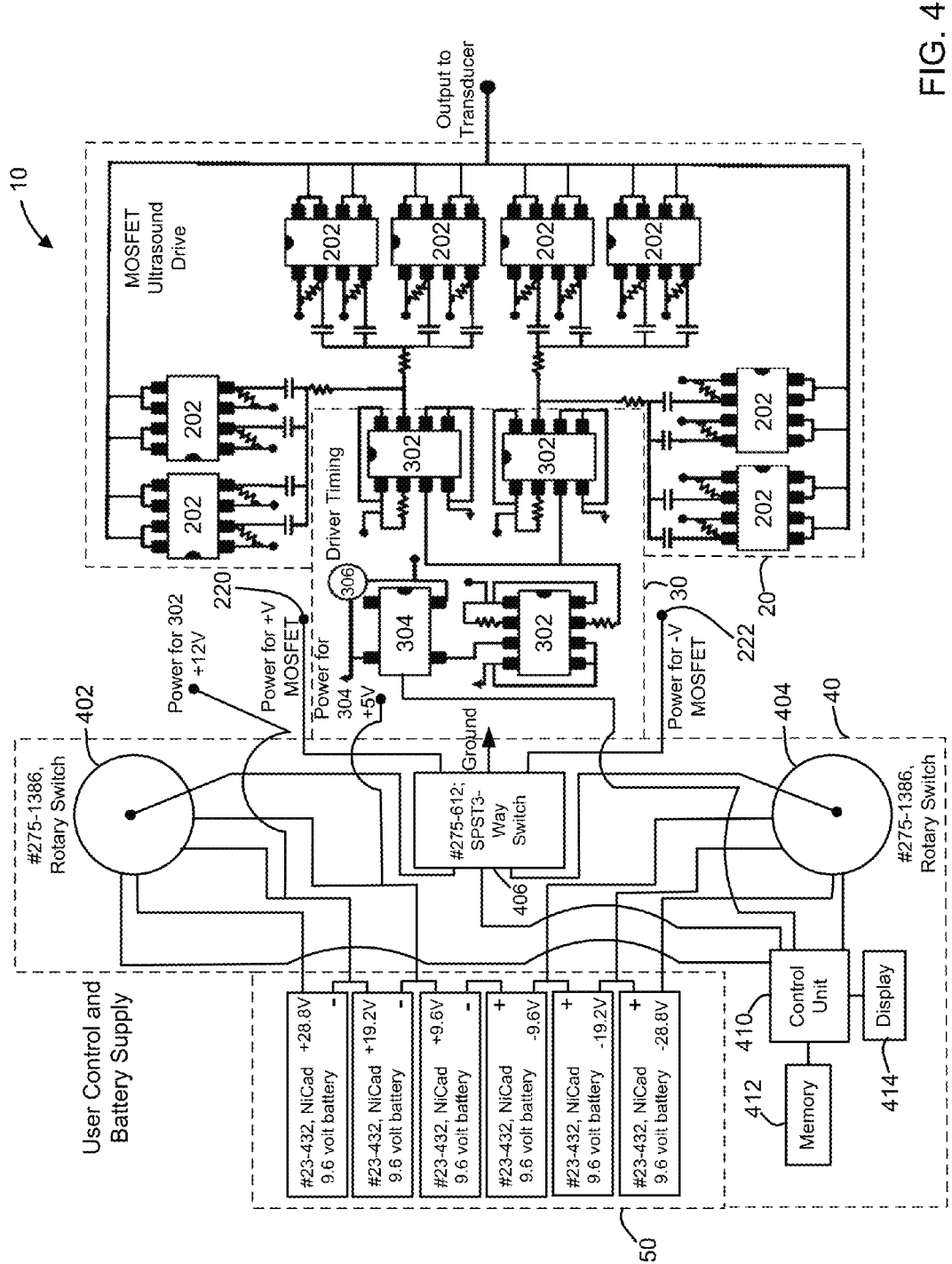
FIG. 4 is a schematic diagram of a power supply having a driver circuit with a plurality of transistor pairs arranged in parallel.

Referring to the embodiment with reference to the block diagram of FIGS. 3 and 4 and the circuit diagram of FIG. 4, the embodiment of FIG. 3 is a scaled up version of the circuit of FIG. 2, scaled up by providing a plurality of transistor pairs as set forth in the embodiment of FIG. 2 in parallel. As shown in the embodiment of FIGS. 3 and 4, driver circuit 20 can include a plurality of such push pull transistor pairs arranged in a parallel configuration. In the embodiment of FIGS. 3 and 4, driver circuit 20 includes eight (8) transistor pairs. However, it will be understood that driver circuit 20 can include 1 to N transistor pairs in parallel, substantially as configured in FIG. 2. Providing a plurality of MOSFET push pull pairs reduces an output impedance of driver circuit 20 and increases the power delivery efficiency of driver circuit 20. With driver circuit 20 provisioned to have an output impedance of less than about 0.5 Ohms, and with transducer 90 having an appropriate impedance 95%-100% of the energy from the power supply 10 can be delivered to transducer 90.

Referring to the embodiment of FIGS. 3 and 4, the Intersil Corporation EL7158ISZ pin driver integrated circuit 302 including a pin driver acts as the logic switch for the MOSFETs that supply the power oscillation drive to the ultrasound transducer. For high power continuous wave applications requiring high current, pin drivers are used to switch MOSFETs in parallel to lower the current burden on each MOSFET. As shown in FIGS. 3 and 4, a single timed pin driver at 5V drives two pin drivers at 12V as a branching cascade to switch four MOSFETs each for the portable high power ultrasound driving system. Each pin driver/MOSFET unit is wired as shown with respect to the single transistor pair embodiment of FIG. 2. Referring to the circuit of FIG. 2, 1 Ohm power output series resistors (not shown) can optionally be included at the output of each transistor pair. With the series resistors, the output impedance of the driver circuit 20 was measured directly, and determined from manufacturer values of the MOSFETs, and the eight 1 Ohm parallel power output series resistors (which can optionally be deleted) to be almost entirely resistive and approximately 0.2-0.3 Ohms. The output impedance can be reduced by removing the power output series resistors. Where driver circuit 20 includes a plurality of transistor pairs, the effective output impedance of the driver circuit 20 can be given by the formula $$R_D = \frac{Rp}{N}$$

where $R_P$ is the output impedance of an individual transistor pair. Thus, where each transistor pair has an output impedance of about 0.5 Ohms, and there are eight (8) pairs, the total output impedance can be expected to be about 0.06 Ohms. Where the output impedance associated with each pair is about 1.5 Ohms, and there are eight (8) pairs, the output impedance of driver circuit 20 would be expected to be about 0.19 Ohms. By scaling up driver circuit 20, via arranging additional transistor pairs in parallel, an output impedance of driver circuit 20 can be reduced to continually lower levels. For example, where an output resistance of an individual transistor pair is 0.5 Ohms, an output impedance resulting by including 16 pairs to parallel would be about 0.5/16=0.03 Ohms. Referring to the circuit of FIGS. 3 and 4 in an additional aspect, a timing of a first set of four transistor pairs is provided by first pin driver integrated circuit and a timing for a second set of four transistor pairs is provided by a second pin driver integrated circuit. Providing such a balanced configuration, where each pin driver integrated circuit that outputs a timing signal that is coupled to a transistor pair, is coupled to an equal number of transistor pairs reduces noise relative to an imbalanced configuration (e.g. one in which a first pin driver integrated circuit provides timing for four transistor pairs, and a second pin driver integrated circuit provides timing for two transistor pairs. Referring to the circuit of FIGS. 3 and 4, while a particular chip layout is described embodying a particular degree of integration, it is understood that alternative scales of integration are possible. For example, the dual MOSFET integrated circuits described can be replaced with four MOSFET integrated circuits. In one embodiment the entirety of circuit components of the driver circuit 20, timing circuit 30, and power distribution and control circuit 40 can be provided on a common integrated circuit.

In the development of apparatus 1000, it was determined that including additional transistor pairs can increase an input capacity of driver circuit 20, thereby decreasing the frequency bandwidth of driver circuit 20. For expanding a frequency bandwidth of power supply 10, power supply 10 can be provisioned as shown in FIG. 5.

Figure 5:
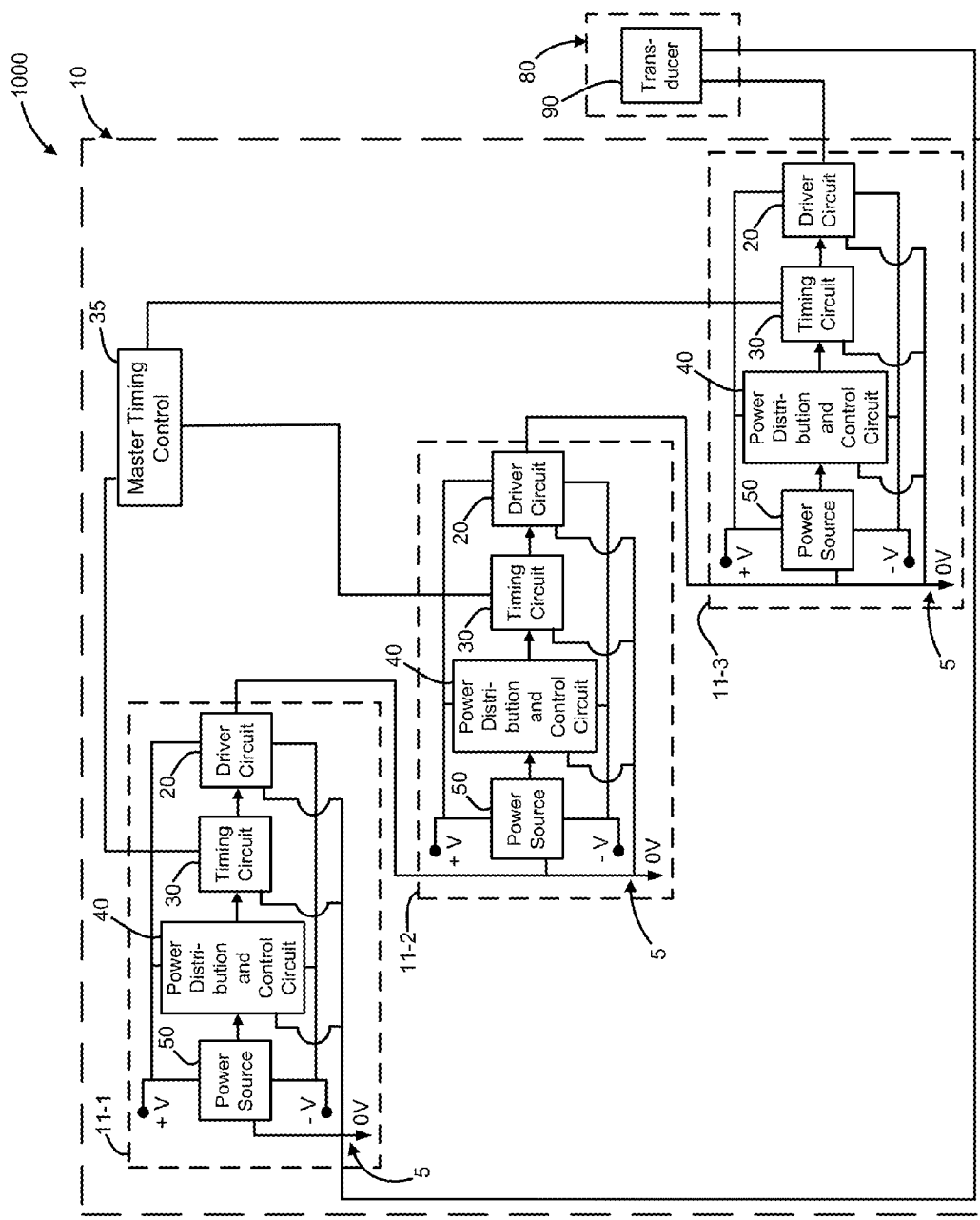
FIG. 5 is a schematic diagram of a power supply having a plurality of series connected power supply stages.

In the embodiment of FIG. 5, power supply 10 can include a plurality of power supply stages 11-1, 11-2, 11-3. Each stage, 11-1, 11-2, 11-3 can include a driver circuit 20, a timing circuit 30, power distribution circuit 40, an associated power source 50, e.g., a battery power source or AC to DC converter and an associated stage ground 5. Providing each stage to have an associated power source that can be isolated from the power sources of remaining stages can be advantageous for a variety of reasons. For example, such arrangement mitigates ground coupling and looping, provides isolated power supply stages for multiple channel transducer drive, and provides power supply backup protection. In the embodiment of FIG. 5, there are three (3) power supply stages. However, power supply 10 could also have 1, 2, or N power supply stages. For connecting the stages, an output of a driver circuit 20 of a first stage, e.g., 11-1 is input into the stage ground 5 of the succeeding stage. That is, an output of stage 11-1 is input into ground 5 of stage 11-2, and the output of driver circuit 20 of stage 11-2 is input into the stage ground 5 of stage 11-3. The stage ground 5 of a first stage 11-1 in the described example can be connected to earth ground.

Providing a plurality of series connected power supply stages as shown in FIG. 5 operates to sum the voltages of the various stages. For example, if each stage is similarly configured and the first stage has an output voltage of ±MV, the output of power supply would be ±NMV where N is the number of stages, and M is the voltage output of each stage. Accordingly, the multiple stage power supply set forth herein is operative to provide the function of a voltage transformer without design complexities and manufacturing obstacles sometimes posed by transformers. In some applications, the incorporation of a transformer is advantageous.

The providing of multiple power supply stages increases a frequency bandwidth of power supply 10 and allows a bandwidth restriction problem associated with disposing transistor pairs in parallel to be overcome. An input capacitance of power supply 10 is reduced as stages are added. For example, if each stage is similarly configured and the first stage has an input capacitance $C_1$, the input capacitance of multiple series power supplies would be N/C where N is the number of stages and C is the input capacitive of each stage.

An effective output impedance of driver circuit 20 of the third stage 11-3 will be the sum of the output impedance of each driver circuit 20 of power supply 10. However, it will be seen that the value of the effective in output impedance can be maintained at a low impedance level by configuring each stage's driver circuit 20 to have a low output impedance. It is seen that where each stage has an output impedance of 0.03 Ohms, (e.g., as in the 16 transistor pair example set forth herein) an effective output impedance of the last stage driver circuit will be under 0.1 Ohms, still providing excellent voltage transfer to the load, even in cases where a transducer has low impedance (e.g., even where the load has an impedance of 1.0 Ohms, a voltage ratio between load and source would be above 90% (90.9%)).

In another aspect, power supply 10 including multiple stages 11-1, 11-2, 11-3 in series can include a master timing control unit 35. Master timing control unit 35 can be isolated from each stage. Master timing control unit 35 can operate to control a frequency at which each power supply stage 11-1, 11-2, 11-3 switches. Master timing control unit 35 can be operative to switch each stage at a certain frequency or at different frequencies. It has been mentioned that each stage 11-2, 11-2, 11-3 can be similarly configured. For example, each stage 11-1, 11-2, 11-3 can have the same number of transistor pairs arranged in parallel. In another example, each stage 11-1, 11-2, 11-3 can have a different number of transistor pairs, each stage having a number of transistor pairs ranging from 1 to N.

The power supply drive circuits set forth in FIGS. 2-4 generally feature low output impedance, a relatively low voltage output signal, and high output current capacity. It has been described that an output impedance of driver circuit 20 can be decreased by providing a plurality of transistor pairs in parallel as shown in the embodiment of FIGS. 3-4. Also, an output current capacity of drive circuit 20 can be increased by providing transistor pairs as shown in the circuit of FIG. 2 in parallel. The output current capacity of driver circuit 20 is approximately the sum total of the output MOSFET output current capacity for each individual transistor pair. For example, in the driver circuit of FIG. 2, the single transistor pair driver circuit, having a transistor pair formed on integrated circuit 302 has an output current capacity of about 10 Amperes. In the embodiment of FIGS. 2-3 having eight (8) transistor pairs arranged in parallel where the pairs are formed on a smaller configured MOSFET integrated circuit, the output current capacity is about 80 Amperes. The output current capacity of driver circuit 20 can be increased or decreased by increasing or decreasing the number or transistor pairs that are arranged in parallel in driver circuit 20. Similarly, an output impedance of driver circuit 20 decreases as additional transistor pairs are added driver circuit 20. In the embodiment of FIG. 2 where driver circuit 20 shows a single transistor pair driver circuit, driver circuit 20 has an output impedance of 0.5 Ohms. In the embodiment of FIGS. 2-3, where driver circuit 20 has eight (8) transistor pairs arranged in parallel and the integrated circuits that are set forth herein, driver circuit 20 has an output impedance of about $$R_D = \frac{Rp}{N} = 0.6 \text{ Ohms}$$

The output impedance of driver circuit 20 can be adjusted to a desired output impedance by increasing or decreasing a number of parallel arranged transistor pairs in driver circuit 20.

According to the maximum power theorem, maximum power is delivered to a load where an impedance of a load is matched to an output impedance of a source. In some embodiments, apparatus 1000 can be configured so that an impedance of a load is matched to an impedance of driver circuit 20. In other embodiments however, load impedance can be mismatched with respect to an impedance of driver circuit 20, which can be provisioned to have a low output impedance (e.g., less than 0.5 Ohms), and apparatus 1000 can be provisioned so that a ratio of an output impedance of driver circuit 20 to a load impedance is less than ⅒. Provisioning an output impedance to be low (e.g., less than 0.5 Ohms) and further so that an output impedance to load impedance ratio is less than ⅒ provides a number of advantages. For example, configuring driver circuit 20 to have a low output impedance and low (e.g., ⅒ or less impedance ratio) results in high energy conversion efficiency. A substantial majority of energy is delivered to the load, (i.e., the transducer 90). As such, very little energy is lost as heat in the driver circuit 20. Such result is particularly advantageous in, e.g., medical applications where heat generated by apparatus 1000 can pose danger to a patient. For any application where power source 50 is provided by one or more batteries, high energy conversion efficiency embodiments set forth herein yield significant advantages in terms of battery life. Maintaining a low driver circuit output impedance and impedance ratio also assures that a source voltage closely corresponds to a load voltage, thus improving the controllability and ease of use of the apparatus. A voltage delivered to a transducer 90 can substantially be set by establishing a source voltage.

Driver circuit 20 as set forth herein can include an associated source voltage when driver circuit 20 is in an active state and when driver circuit 20 outputs a drive signal having a frequency, e.g., to a resonant frequency of transducer 90. A driver circuit source voltage can be measured directly by measuring voltage across output terminal of a driver circuit in an open circuit condition (without current flow there is no voltage drop across the driver circuit's impedance contributing components). Further, with a load attached across the output terminals of a driver circuit, and with the driver circuit driving the load, e.g., at a frequency corresponding to the resonant frequency, the voltage at the load can be expressed as $$V_{Load} = \frac{V_{Source} R_{Load}}{R_{Source} + R_{Load}} \quad \text{Eq. 1}$$

where $R_{Source}$ is the output impedance of driver circuit 20. Accordingly, the ratio of a voltage across a load (the transducer), to a source voltage can be expressed as $$V_{Load}/V_{Source} = \frac{R_{Load}}{R_{Load} + R_{Source}} \quad \text{Eq. 2}$$

Thus, it is seen that as the output impedance of the driver circuit 30 tends to zero, the load voltage more closely approximates the source voltage. Further, it is seen that by configuring apparatus 1000 so that the ratio of the source output impedance to the load impedance is maintained at or below ⅑, the amplitude of voltage across the load relative to the amplitude of the source voltage at the driver circuit will remain at or above 90 percent. Various embodiments of apparatus 1000 having such ratio are set forth herein. In other embodiments set forth herein, a voltage ratio of load to source is at or above 95% and in other embodiments is at or above 99%. Prospective examples with expected associated data are set forth in Table A below.

TABLE A

| Embodiment | Driver Circuit Output Impedance | Transducer Impedance | Load To Source Voltage Ratio |
|---|---|---|---|
| 1 | 0.5 Ohms | 8 Ohms | 94.1% |
| 2 | 0.03 Ohms | 1 Ohm | 97.1% |
| 3 | 0.5 Ohms | 5 Ohms | 90.9% |
| 4 | 0.09 Ohms | 3 Ohms | 97.1% |
| 5 | 0.03 Ohms | 10 Ohms | 99.7% |

Figure 7:
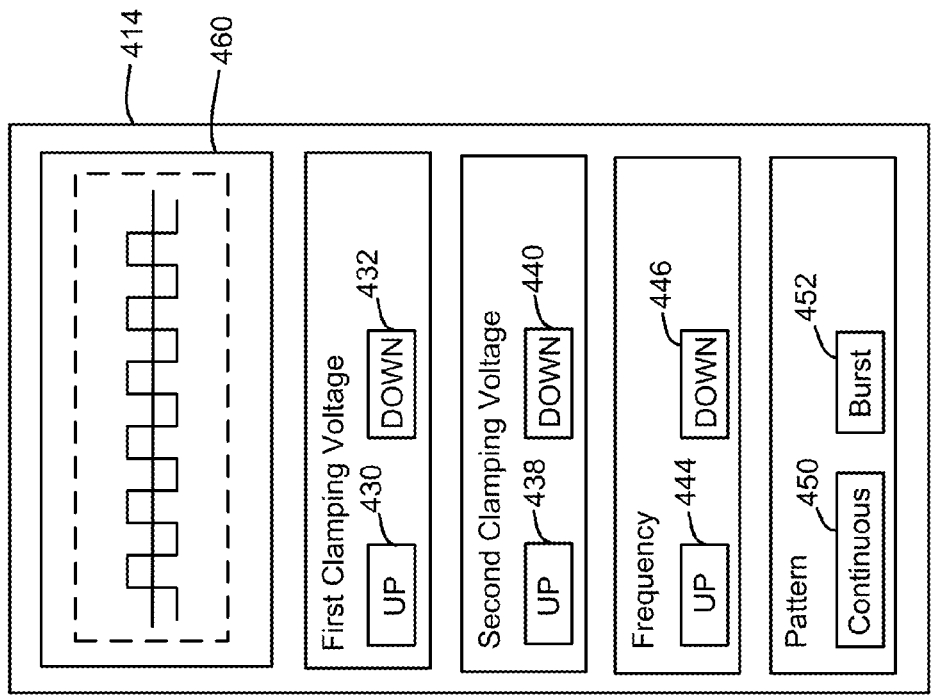
FIG. 7 is a depiction of an exemplary user interface component of an ultrasound wave generating apparatus, wherein actuator virtual control buttons are displayed on a display of an ultrasound wave generating apparatus.

Another advantage of configuring driver circuit 20 to include a low output impedance and low impedance ratio is that such configuration reduces an amount of shift in a resonant frequency of transducer 90. Referring to FIG. 7, there is shown a plot of the resonant frequency of transducer 90 (the frequency of a drive signal output by driver circuit 20 at which maximum power is output by ultrasound transducer 90) versus source output impedance of driver circuit 20. As the source output impedance increases, the resonant frequency shifts significantly (from about 1.51 MHz to about 1.63 MHz in the described example). Reducing the amount of resonant frequency shift by reducing the source output impedance improves controllability and ease of use of apparatus 1000 for the reason that a resonant frequency that is observed for a particular transducer is more proximate a nominal frequency of resonance for the particular transducer (normally provided by a manufacturer of the transducer and determined based on material properties of transducer 90).

Referring to additional advantages of the low output impedance high output current configuring driver circuit 20, a high output current capacity at driver circuit 20, about 50 Amperes or more in some embodiments (while low current output capacity embodiments are advantages in certain applications) allows high energy output at transducer 90 (about 50 Watts or more in some embodiments) with modest voltages of less than 100V, and in several embodiments, about 50V or lower or 25V or lower. Such functionality (high energy output with only modest voltages) is advantageous in numerous applications, including in medical applications where risk of harm to a patient or caregiver in proximity to transducer 90 is posed by exposure to high voltages, e.g. of 100V or more. In some applications, however, an output of over 100V is advantageous.

In one embodiment, ultrasound wave generating apparatus 1000 can be a single mode apparatus, which has a fixed (non-interchangeable) transducer 90 and which outputs a drive signal of the same characteristic each time it is activated for output of a drive signal. In another embodiment, ultrasound wave generating apparatus 1000 can be a multiple mode apparatus capable of output of drive signals of different characteristics at different times. Apparatus 1000 can be operative so that apparatus 1000 outputs a drive signal having a different set of characteristics in response to an operator input control that is input into a user interface of apparatus 1000. Apparatus 1000, where provisioned so that a transducer assembly thereof is one of a plurality of replaceable candidate transducer assemblies, can be operative so that apparatus 1000 outputs a different output drive signal having a different set of characteristics responsively which of the candidate transducer assemblies is presently associated to power supply 10.

Power distribution and control circuit 40 in the embodiment of FIG. 4 can include a three-way switch integrated circuit 404. Switch integrated circuit 404 can be manually moved by an operator to switch the switch integrated circuit 404 between an OFF position and an ON position. In the ON position, power from power source 50 is coupled to the clamping voltage terminals of driver circuit 20. Power supply ground can be used to isolate +5V and +12V supplies, thus reducing a wiring burden. In another aspect, power distribution and control circuit 40 can include a control unit 410. Control unit 410 can be provided by a microcontroller or a microprocessor. Control unit 410 can be associated with memory 412, which can store various data, program data, and setup data for determining characteristics of an output signal output by driver circuit 20. Control unit 414 can be in communication with display 414, which can be configured to have user interface capability.

For illustrating additional features including control features of apparatus 1000, FIG. 4 shows a further detailed schematic of a power supply shown in the block view of FIG. 3. In FIG. 4, there is shown driver circuit 20, timing circuit 30, power distribution and control circuit 40, and power source 50. Power source 50 in one embodiment can include a plurality of 9.6V, 1600 mA h NiCad rechargeable battery packs. Power source 50 in another embodiment can include an AC to DC converter for coupling to an AC wall outlet power source. The battery packs can be, e.g. No. 23-432 battery packs available from RadioShack Corporation. Power supply 10 can also include rotary switches 402 and three-way switch 404 forming power distribution and control circuit 40. The user can adjust power delivery to the transducer through the MOSFETs in 9.6V increments over the range ±28.8V. Additional batteries can be included for increasing the voltage range of power source. A blue "on" LED 306 in the embodiment of FIG. 4 is tied into the on/off switch that supplies power to the crystal oscillator integrated circuit 304 and pin driver integrated circuits 302 through 5V and 12V 1 A voltage regulators that also have bypass capacitors. The output of the device is terminated in a male Bayonet Neill Concelman (BNC) connector on the front panel. A battery recharge port at the back of the system (not shown) is wired to charge the six battery packs in series. To charge the system, the device is switched to the off position and the rotary switches are moved to a non-connected terminal as labeled on the devices panel.

A user interface of ultrasound wave generating apparatus 1000 can be partially provided by switch 402 and switch 404 which can be used by an operator to control voltages at clamping voltage terminals 220, 222 and can be partially provided by switch 406. A user interface of ultrasound wave generating apparatus 1000 can also include additional control actuators. For example, apparatus 1000 can be configured so that display 414 displays various virtual control buttons which can be actuated by an operator. One example of apparatus 1000 where display 414 is configured to include an interface control button is shown in FIG. 7.

In the example at FIG. 7, apparatus 1000 can be operative so that buttons 430, 432 can be used to adjust a voltage at first clamping voltage terminal 220, buttons 438, 440 can be used to control a voltage at second clamping voltage terminal 222, buttons 444, 446 can be used to control a frequency of a drive signal output by driver circuit 20, and buttons 450, 452 can be used to control a pattern of low output drive signal, e.g., to select between a "continuous pattern" or a "burst pattern." In the embodiment set forth herein, control unit 410 can be in communication with switches 402 and 404 so that a voltage at clamping voltage terminals 220, 222 can be adjusted either with use of voltage switches 402, 404 or buttons 430, 432, 438, 440. In preview area 460, there can be displayed a representation of the output drive signal expected to be output when the present set of control parameters is applied. For control of output drive signal frequencies with use of a user interface, control unit 410 can be communicatively coupled to timing device 304 as is indicated in the schematic drawing of FIG. 4. Timing devices such as the crystal oscillator integrated circuit specifically set forth can be selected to be programmable, so that a frequency within a range of frequencies can be selected via input of a control to the device. For expansion of the range of selectable frequencies, a plurality of timing devices having overlapping frequency of ranges can be included in timing circuit 30. Appropriate multiplexing circuitry (not shown) can be provided for allowing selection of an appropriate timing device based on a selected frequency.

In some embodiments of apparatus 1000 where transducer 90 is one of a plurality of candidate replaceable transducers incorporated in one of a plurality of respective transducer assemblies, an output drive signal of apparatus 1000 can be responsive to which transducer assembly (e.g. with reference to FIG. 1, transducer assembly A or transducer assembly B), is presently associated to power supply 10. In the specific embodiment described replaceable transducer assemblies A and B incorporate transmission line 70 and probe 80. However, in another embodiment, replaceable parts of apparatus 1000 that incorporate a transducer (i.e., the transducer assembly) can incorporate probe 80 only with transmission line 70 being a fixed component part. In another embodiment, a transducer assembly incorporating transducer 90 can comprise essentially only transducer 90. A transducer assembly that consists essentially only of transducer 90 can be provided as a plug in component of a circuit board. To the end that apparatus 1000 can adjust characteristics of an output drive signal responsively to which of a plurality of candidate transducer assemblies is presently associated to power supply 10, each candidate transducer assembly can have an associated memory 900 (see FIG. 1) storing an identifier for the transducer, e.g., in the form of a text based alpha numeric identification number. As shown in FIG. 1 memory 900 can be housed within housing 82 of probe 80.

Apparatus 1000 can be operative so that when a new transducer assembly (e.g., A, B and another assembly, C, etc.) is associated to power supply 10, the transducer assembly identifier information stored in memory 900 is communicated to control unit 410, via appropriate communication apparatus 902. For example, control unit 40 and memory 900 can be in communication via a communication apparatus 902 provided by a two wire interface, e.g., a Phillips I²C bus. Control unit 410 can be operative so that responsively to identification data being communicated between memory 900 and control unit 410, control unit 410 establishes appropriate settings for output of a drive signal having a specific set of characteristics for driving the ultrasound transducer of the specific transducer assembly presently associated to power supply 10.

Hereinabove, it has been described that output drive signal characteristics of an output drive signal can be made responsive to an associated transducer assembly by way of communicating of data respecting an identity of a transducer assembly. In another embodiment, apparatus 1000 can be operative so that output drive signal characteristics output by driver circuit 20 are responsive to an associated transducer by way of being controlled with use of specific timing circuitry associated to the transducer assembly of a set of candidate transducer assemblies.

In one example, as explained with reference to FIG. 1, each transducer assembly of a set of candidate transducer assemblies (which may or may not be the full set of candidate transducer assemblies) can be provided with an associated timing device. As shown in FIG. 1, a crystal oscillator integrated circuit 304 can be associated to transducer assembly A, and crystal oscillator integrated circuit 304 can be associated to transducer assembly B. Each crystal oscillator integrated circuit 304 can have associating communication apparatus 305 for communicating with remaining components of timing circuit 30. Communication apparatus 305 can comprise a copper wire. Apparatus 1000 can be operative so that when a new transducer assembly is associated to power supply 10, a timing device associated to the new transducer assembly is made active to control one or more output characteristics of the output drive signal. Referring to the example in FIG. 1, apparatus 1000 can be operative so that when transducer assembly A is associated to a power supply 10, timing device 304 of transducer assembly A controls a timing of the output drive signal. Apparatus 1000 can also be operative so that when the transducer assembly B is associated to power supply 10, timing device 304 disposed with transducer assembly B controls a timing of the output drive signal output by drive circuit 20.

Reference will now be made to ultrasound transducer 90 of probe 80. Ultrasound transducer 90 of probe 80 can be provided by a PZT-4, 1.54 MHz, and 0.75 in. diameter piezoelectric ceramic with a radius of curvature of 1.5 of the type available from EBL Products, Inc. Such transducer by EBL Products, Inc. is given a nominal frequency of resonance of 1.5 MHz by the manufacturer. Housing 82 can be provided by a polyvinyl chloride (PVC) ergonomic plastic assembly. Such assembly can be custom built using a micro-lathe and milling system of the type available from Sherline Products, Inc. The clear acrylic front of the housing 82 acts as a protective cover to the ceramic transducer 90 and also functions as an in-plane focal alignment standoff for the ultrasound energy emitted by transducer 90. Regarding referenced elements herein, a reference to element "90" herein will be regarded as a reference to any of specific transducers referenced herein, e.g., transducer 90, 90A, 90 90B, and so forth.

Figure 8:
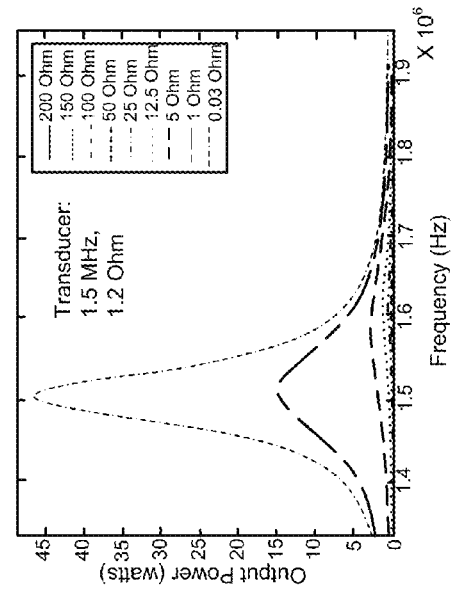
FIG. 8 is a Mason model power output chart for an ultrasound transducer in one embodiment; where the ultrasound transducer is provided by a 10.3 Ohm ultrasound transducer having a nominal frequency of resonance of 1.5 MHz.
Figure 9:
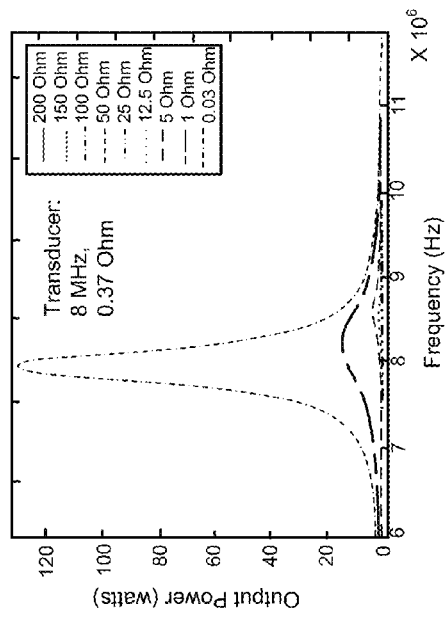
FIG. 9 is a Mason model power output chart for an ultrasound transducer in one embodiment; where the ultrasound transducer is provided by a 1.2 Ohm ultrasound transducer having a nominal frequency of resonance of 1.5 MHz.
Figure 11:
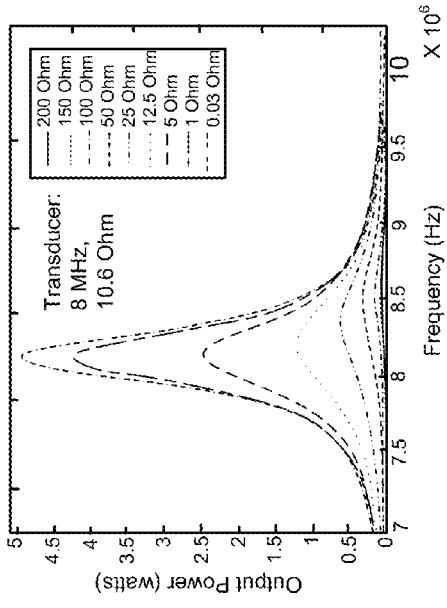
FIG. 11 is a Mason model power output chart for an ultrasound transducer in one embodiment; where the ultrasound transducer is provided by a 0.37 Ohm ultrasound transducer having a nominal frequency of resonance of 8 MHz.
Figure 12:
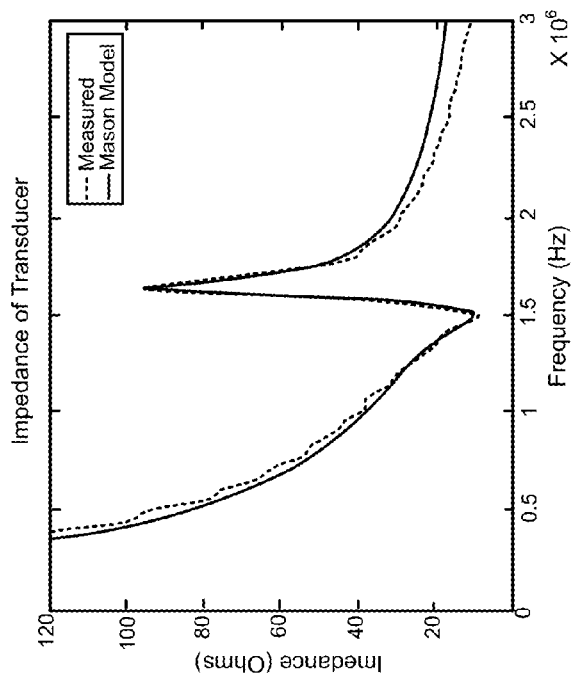
FIG. 12 is an impedance versus frequency plot for a selected ultrasound transducer in one embodiment.

Transducer 90 can be wired with use of a transmission line 70 provided by a 22 gauge coaxial cable terminated with a connector 72 (FIG. 21) which can be provided by female BNC connector. Transducer 90 can have power output characteristic as shown in FIGS. 8, 9, 10, and 11, and impedance characteristics as shown in FIG. 12. In FIGS. 8, 9, 10, and 11, there is shown a maximum power output curve, for various transducers calculated using the Mason Model, while being driven by differently configured driver circuits having different output impedances over a range of frequencies. FIG. 8 is a power output plot for a transducer having a nominal frequency of resonance of 1.5 MHz and an impedance of 10.3 Ohms. FIG. 9 is a power output plot for a transducer having a nominal frequency of resonance of 1.5 MHz and an impedance of 1.2 Ohms. FIG. 10 is a power output plot for a transducer having a nominal frequency of resonance of 8 MHz and an impedance of 10.6 Ohms. FIG. 11 is a power output plot for a transducer having a nominal frequency of resonance of 8 MHz and an impedance of 0.37 Ohms. A resonant frequency of ultrasound transducer 90 can be regarded as the frequency at which the ultrasound transducer emits maximum power when driven by the output drive signal output by driver circuit 20 that is to drive the transducer.

Figure 6:
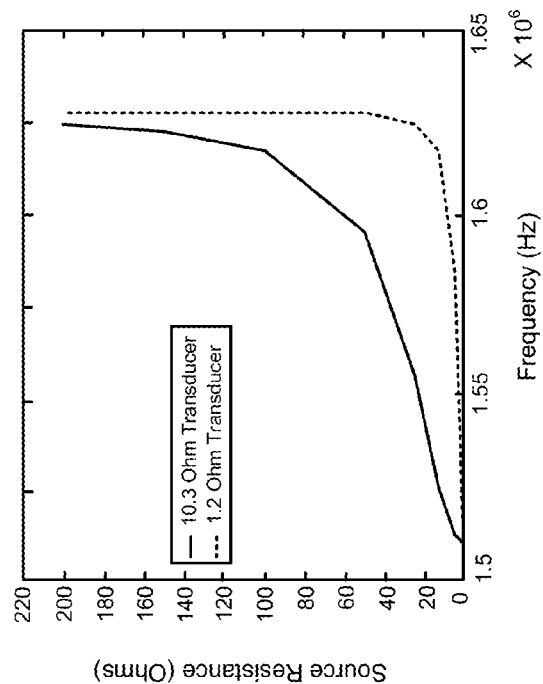
FIG. 6 is a plot of resonant frequency (expressed as a point value) versus driver circuit output impedance for illustrating an effect of driver circuit output impedance on resonant frequency.

Referring to FIG. 6, and again with reference to power output plots of FIGS. 8, 9, 10, and 11, it is seen that a resonant frequency will shift slightly as an output impedance of driver circuit 20 is increased. Regarding "resonant frequency" as referred to herein, it is understood that a number of factors can contribute to a transducer's resonant frequency, e.g., the output impedance of the driver circuit 20, the impedance of transmission line 70. Nevertheless, as the primary determinants of the frequency at which transducer 90 resonates are the material properties of transducer, the reference to "resonant frequency of the transducer" is appropriate. Also, if an output impedance of driver circuit 20 and transmission line 70 are maintained at approximately low levels, the contribution of the driver circuit output impedance, and the impedance of transmission line impedance will be negligible.

In FIG. 12, there is shown an impedance versus frequency curve for the noted PZT-4, 1.5 MHz (nominal frequency of resonance), 8.0 Ohm transducer. Impedance characteristics of a ceramic transducer can be measured, e.g., with use of a standardly known meter method for measuring impedance. In the described example for transducer 90, an impedance of transducer 90 is at its lowest value of about 8.0 Ohms at an impedance measurement equipment frequency of about 1.5 MHz. The impedance measuring equipment frequency at which an impedance of transducer 90 is at its lowest value with reference to FIG. 12 can be regarded as a measurement of the resonant frequency of transducer 90. However, as noted, the resonant frequency of transducer 90 when driven by driver circuit 20 can be expected to be dependant, in part, on characteristics of driver circuit 20. By definition, when driven at the resonant frequency power output of transducer 90 is at its highest level. A resonant frequency can be expressed as a point value (e.g., 1.54 MHz) or as a range of frequencies at which power output is above a predetermined percentage (e.g., 90%) of a maximum power output value. A drive frequency corresponding to the resonant frequency can be regarded as a frequency of about the resonant frequency as expressed at a point value. A drive frequency corresponding to the resonant frequency can also be regarded as a frequency within a resonant frequency range, where a resonant frequency is expressed as a frequency range.

It has been noted that power supply 10 can be operative so that an output drive signal for driving transducer 90 can have a frequency corresponding to the resonant frequency of transducer 90. In another aspect, power supply 10 can be configured so that an output drive signal output by power supply 10 for driving transducer 90 can oscillate between a positive and negative voltage.

Provisioning power supply 10 to output a drive signal for driving transducer 90 that includes both positive and negative polarity provides significant advantages. Referring to transducer 90, transducer 90 in general will compress when a voltage of a first polarity is applied thereto and will expand when a voltage of a second polarity is applied thereto. Accordingly, applying a drive signal with positive and negative polarity provides variation in the stresses that are applied to transducer 90 for causing emissions of ultrasound waves, thereby increasing the life of transducer 90. In another aspect, providing a driver signal with oscillating positive and negative polarity results in any standing voltages of transducer 90 cancelling and thereby reducing a magnitude of standing voltages. Still, further use of a bipolar output drive signal allows use of both positive and negative channels of a transistor pair (e.g., transistor 204, transistor 206 as shown in FIG. 2) reducing thermal fatigue of the transistor pair and increasing the current output capacity of the transistor pair, thereby allowing higher power output with reduced voltage below hazardous levels. (It will be seen that a ±50V signal applied to a load produces the same output power as a ±0-100V drive signal, but with substantially safer voltage levels).

Referring to Table B, various prospective examples of transducer assemblies are summarized in connection with exemplary drive signals associated with each transducer assembly.

TABLE B

| Transducer Assembly | Transducer | Resonant Frequency (Expressed As Point Value) | Resonant Frequency (Expressed As Range At Which Power Conversion Efficiency Is 90% Of Maximum) | Nominal Frequency of Resonance (Normally Provided By Manufacturer) | Impedance of Transducer (As Measured Utilizing Impedance Measuring Equipment) | Exemplary Drive Signal |
|---|---|---|---|---|---|---|
| A | 90A | 1.54 MHz | 1.47-1.58 MHz | 1.5 MHz | 8 Ohms | Continuous Imbalanced Bipolar Square Wave at about 1.54 MHz |
| B | 90B | 1.01 MHz | 0.95-1.09 MHz | 1 MHz | 14 Ohms | Continuous Balanced Square Wave at 1.01 MHz |
| C | 90C | 2.60 MHz | 2.45-2.68 MHz | 2.5 MHz | 5 Ohms | Continuous Unipolar Sinusoidal Wave At 2.60 MHz |
| D | 90D | 3.11 MHz | 3.01-3.22 MHz | 3 MHz | 7 Ohms | Continuous Imbalanced Bipolar Sinusoidal At 3.11 MHz |
| E | 90E | 7.55 MHz | 2.51-11.56 MHz | 7.5 MHz | 15 Ohms | Burst Balanced Bipolar Square Wave at 7.55 MHz |
| F | 90F | 1.52/4.15/6.51 | 1.45-1.59/3.85-4.35/6.37-6.62 MHz | 1.5/4/6.5 | 3 Ohms | Continuous frequency sweeping signal at 1.52 MHz (bipolar imbalanced), 4.15 MHz (bipolar imbalanced), 6.51 MHz (bipolar imbalanced) |

In another aspect, power supply 10 can be operative to output an imbalanced bipolar signal for driving transducer 90. An "imbalanced" bipolar signal herein can have, in one embodiment, an amplitude difference between first and second polarities of 1V or greater (e.g., a +10V to −9V imbalanced bipolar signal); in another embodiment, 5V or greater (e.g., a +5V to −10V imbalanced bipolar signal); in another embodiment, 20V or greater (e.g., a +100V to −80V imbalanced bipolar signal); and in another embodiment, 40V or greater (e.g., a +30V to −70V imbalanced bipolar signal). In the development of apparatus 1000, it was determined that the capacity of transducer 90 to withstand forces imparted thereto is increased with reference to compression forces relative to expansion forces. Transducer 90 will be compressed when a negative voltage drive signal is applied thereto and expanded when a positive voltage drive signal is applied thereto (or alternatively, depending on the setup, compressed when a positive voltage drive is applied and expanded when a negative voltage drive signal is applied). Nevertheless, driving transducer 90 with both positive and negative voltage drive signals advantageously produces variations of the range of motion of transducer 90. By provisioning power supply 10 to output an imbalanced bipolar drive signal, both compression and expansion forces can be imparted to transducer 90, and yet compression forces can be imparted to transducer 90 in greater magnitude than expansion forces.

Referring again to FIG. 4, the provisioning of apparatus 1000 so that both positive clamping terminal voltage and a negative clamping terminal voltage can be independently adjusted via operator input controls input using a user interface of apparatus 1000, allows the output drive signal output by drive circuit 20 to be precisely tuned to the limits imposed by the physical properties of transducer 90 without exceeding such levels.

Characteristics of a suitable output drive signal associated with the transducer assemblies A, B, C, D, E, and F are summarized in FIGS. 13, 14, 15, 16, 17, and 18. In the illustrative Table B and in associated FIGS. 13-18, the output drive signal is shown as being identical (to two decimal points) to the resonant frequency of transducer 90 It will be understood that due to tolerances, an actual drive signal can correspond to a resonant frequency without being identical to the resonant frequency.

Figure 13:
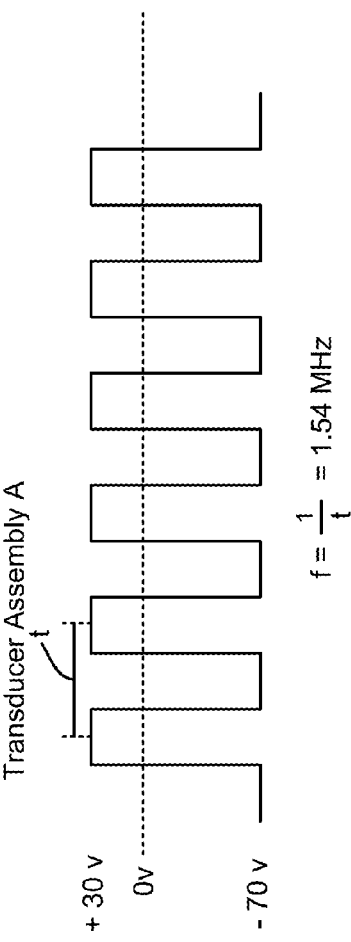

Referring to FIG. 13, imbalanced bipolar output drive signal is shown having a possible voltage peak of +30V and a negative voltage peak of −70V. The output drive signal of FIG. 13 is operative to result in compression force being imparted to transducer 90 in greater magnitude than expansion forces. Apparatus 1000 can be provisioned so that the characteristics of the drive signal of FIG. 13 can be set either responsively to operator control using a user interface of apparatus 1000 or responsively to a particular transducer assembly being associated to power supply 10. In the case where apparatus 1000 is operative to output a drive signal of particular characteristics responsively to association of a particular transducer assembly, e.g., A, B, C, D, E, F, apparatus 1000 can further be operative so that characteristics of the drive signal can be further subject to change via control inputs that are input by an operator using a user interface of apparatus 1000 after the association is completed.

FIGS. 13, 14, 15, 16, 17, and 18 illustrate drive signals that can be set responsively to control inputs that are input by an operator using a user interface of apparatus 1000 and/or responsively to a particular transducer assembly being associated to power supply 10. Characteristics of the drive signal of FIG. 13 have been characterized herein above. Referring to the output drive signal of FIG. 14, the output drive signal of FIG. 14 is a balanced bipolar output drive signal suitable for driving transducer assembly B transducer assembly having transducer 90, 90b. Referring to FIG. 15, the output drive signal of FIG. 15 is a unipolar sinusoidal output drive signal suitable for driving transducer assembly C having transducer 90, 90c. Referring to FIG. 16, the output drive signal of FIG. 16 is an imbalanced bipolar sinusoidal drive signal suitable for driving transducer assembly D having transducer 90, 90d. Referring to the output drive signals of FIGS. 13-16, the output drive signals of FIGS. 13-16 can be regarded as "continuous" drive signals by virtue of their lack of repeated null periods between periods of oscillation. The drive signal of FIG. 17 can be regarded as a burst signal by virtue of it having null periods, $p_n$, intermediate of periods of oscillation. In some applications, e.g., imaging, apparatus 1000 can be operative to output null periods, $p_n$, intermediate of periods of oscillation for purposes of conserving power, where null periods, $p_n$, will not negatively impact function of apparatus 1000. In some imaging apparatuses, for example, it is only necessary that periods of oscillation be timed with exposure periods.

It is seen that apparatus 1000 can be configured so that a switching between transducer assemblies of apparatus 1000 causes switching between modes of operation of apparatus 1000. For example, with transducer assembly A associated, apparatus 1000 can operate in a mode in which apparatus 1000 outputs an imbalanced bipolar drive signal. Apparatus 1000 can further be configured so that a mode of operation of apparatus 1000 changes responsively to a presently associated transducer assembly being switched, e.g., to a mode of operation in which bipolar balanced drive signal (when transducer assembly B is associated), or to a mode of operation in which a unipolar drive signal is output (when transducer assembly C is associated).

In one embodiment, as shown in FIG. 19, transducer 90 can be provided by a single transducer element, e.g., a single transducer disk 91 having a certain impedance and nominal frequency of resonance. In one embodiment, as shown in FIG. 20, transducer 90 can include plural transducer elements, e.g., a plurality of transducer disks arranged in series. In a particular embodiment, each of transducer elements (e.g., ceramic disks) can have a particular associated nominal frequency of resonance and a particular resonant frequency when driven by a driver circuit 20 of a certain configuration. In the example of FIG. 20, transducer 90 includes three (3) transducer elements 91. However, transducer 90 could also include, e.g., two (2) transducer elements, or N transducer element.

Referring to Table B, transducer assembly F illustrates the use case where a transducer assembly includes a transducer comprising a plurality of transducer disks, each having a different nominal frequency resonance and resonant frequency. Each of the elements can comprise a transducer disk of the PZT series of transducer elements available from EBL Products. Such a transducer can be advantageously driven with a drive signal as shown in FIG. 18. The drive signal of FIG. 18 is a frequency sweeping drive signal having a changing frequency. During period $p_1$, the drive signal has a frequency of 1.52 MHz corresponding to the resonant frequency of the first transducer element. During period $p_2$, the drive signal has a frequency of 4.15 MHz corresponding to the resonant frequency of the second transducer element. During period $p_3$, the drive signal has a frequency of 6.51 MHz corresponding to the resonant frequency of the third transducer element of transducer 90F.

Figure 23:
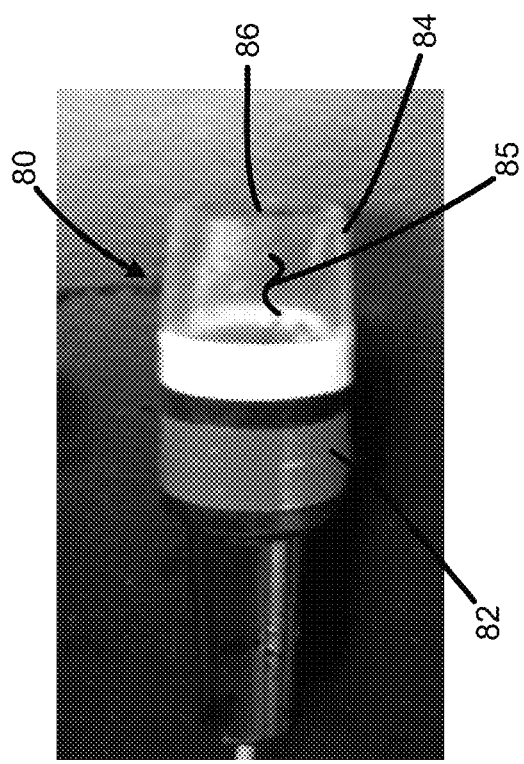
FIG. 23 is a photograph of probe for an ultrasound wave generating apparatus.
Figure 22:
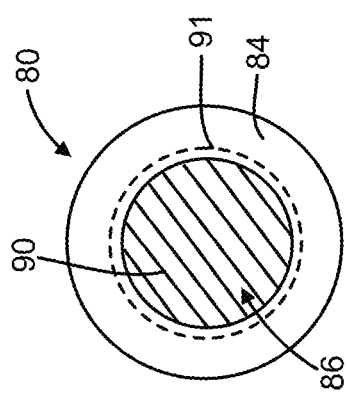
FIG. 22 is a front view of probe for an ultrasound wave generating apparatus.

A physical form view of ultrasound generator 1000 is shown in FIG. 21. Power supply 10 can be small and lightweight, e.g., about 5 pounds. Housing 12 for power supply 10 can have dimensions of about 4×6×2 in.$^3$. Housing 82 for probe 80 can be provided by a polyvinyl chloride (PVC) ergonomic plastic assembly. Referring to housing 82, ultrasound transducer 90 (shown dashed in) can be housed at a distal end of housing 82 as shown in FIG. 21 and standoff component 84 can be disposed to extend from the distal end of housing 82. Standoff component 84 can define a cavity 86. Cavity 86 can be adapted to receive a coupling medium. A coupling medium such as ultrasound fluid or water can be disposed within cavity 86. A suitable ultrasound fluid coupling medium is No. NTNMAA001X ultrasound fluid available from The National Medical Association (NMA). In some applications, probe 80 of apparatus 1000 can be adapted so that standoff component 84 can be replaceably removed from housing 82. Further, standoff component 84 can be provided as one of a family of candidate standoff components which can include, e.g., component 84' and 84". Standoff component 84 can include a light transmissive wall 85. As is best seen in the view of FIG. 23, light transmissive wall 85 can be light transmissive to allow visual viewing into an interior of cavity 86. As shown in the front view of FIG. 22, with transducer periphery 91 dashed in, a periphery of standoff component 84 can be substantially aligned with a periphery of standoff component 84 at the interface between the transducer 90 and standoff component 84. Light transmissive wall 85, as best seen in FIG. 23, permits an operator to view an interior of cavity 86 to determine, e.g., the quality of a coupling medium disposal within cavity (e.g., whether the coupling medium is substantially free of bubbles). Light transmissive wall 85 can be formed partially about the periphery of standoff component 84. In the embodiments of FIG. 23, light transmissive wall 85 is formed entirely about the periphery of standoff component 84. Transmission line 70 can have a length of about 1 m. In another embodiment, transmission line 70 can be deleted and power supply 10 and transducer 90 can be housed in a common housing.

Figure 24:
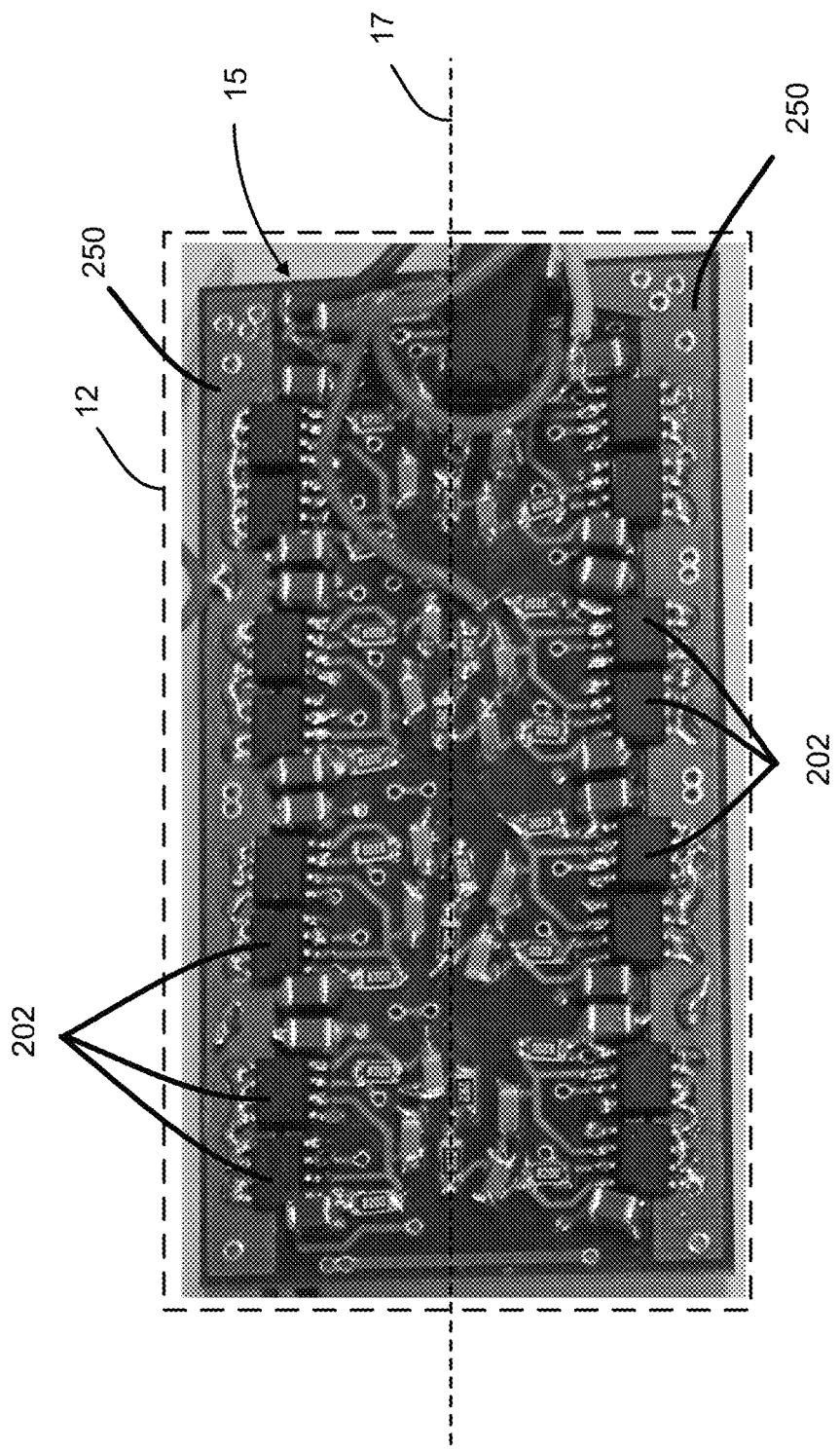
FIG. 24 is a top view of a printed circuit board carrying components of a power supply in one embodiment.
Figure 25:
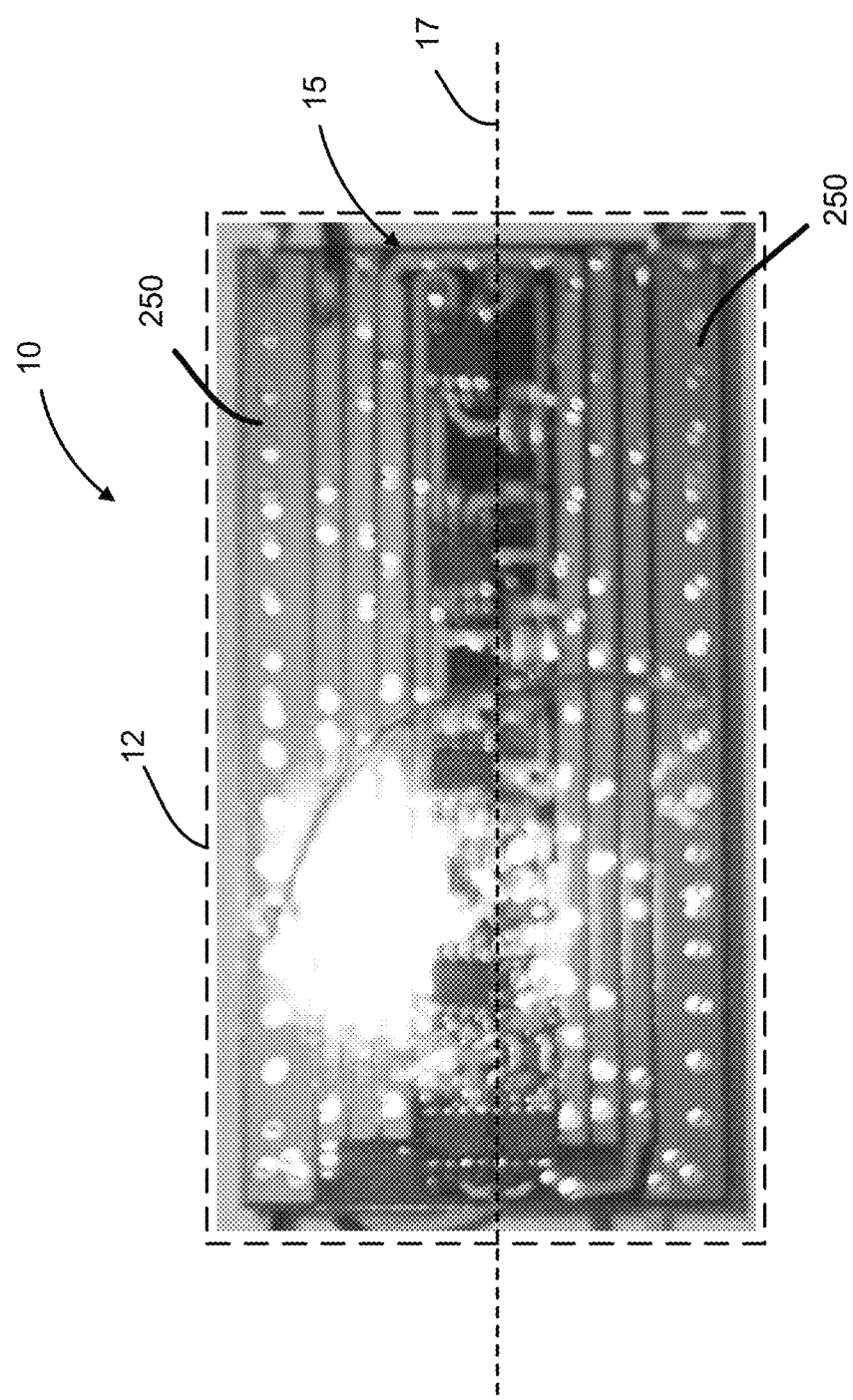
FIG. 25 is a bottom view of the printed circuit board as shown in FIG. 24.

Additional housing and packaging features of apparatus 1000 in one embodiment are set forth with reference to FIGS. 24 and 25. FIGS. 24 and 25 show top and bottom views of a printed circuit board 15 carrying MOSFET integrated circuits 202 of driver circuit 20. In the views of FIGS. 24 and 25, the dashed in border 12 indicates a location of housing 12 when printed circuit board 15 is disposed in housing 12. In the embodiment of FIG. 24, MOSFET integrated circuits 202 can be distributed at an outer periphery of circuit board 15 so that integrated circuits 202 are more proximate a periphery of printed circuit board 15 than a longitudinally extending imaginary center axis 17 of printed circuit board 15. In the embodiment of FIGS. 24 and 25, each MOSFET integrated circuit 202 of driver circuit 20 is so located. Distributed as described proximate housing boundary 12 heat generated by integrated circuits 202 is more likely to be conducted to an exterior of housing 12, thus removing heat from integrated circuits 202 and increasing the power output capacity of MOSFET integrated circuits 202 and of driver circuit 20.

Referring to the circuit diagrams of FIGS. 24 and 25, an output of driver circuit 20 can include an output from each of a plurality of MOSFET integrated circuits co-located at a common node 250. As seen in the physical form view of FIGS. 24 and 25, common node 250 can be physically constituted by a planar configured output voltage plane. Common node 250 configured as an output voltage plane can be distributed over a two dimensional area of printed circuit board 15 to partially define one or more surfaces of printed circuit board 15. In the embodiment of FIGS. 24 and 25, the output voltage plane is distributed to partially define each of a top surface and a bottom surface of printed circuit board 15. As shown, the common node 250 where provided by an output voltage plane can include a planar surface exposed to an exterior or printed circuit board 15. The common node 250 where provided by an output voltage plane as shown in FIGS. 24 and 25 can be formed from a printed circuit board copper surface laminate that is appropriately etched and provided to commonly connect the respective outputs of the various transistor pairs of driver circuit 20. With a common node 250 being constituted with a planar conductor defining a surface of printed circuit board 15 significant heat is removed from the circuit components of apparatus 1000 including from MOSFET integrated circuits 202 of driver circuit 20 thus increasing a power output capacity of MOSFET integrated circuits 20. Common node 250 where provided by an output voltage plane can be distributed such that the output voltage plane is in thermal contact or near thermal contact with an electrically insulative portion of a plurality of (and in one embodiment each) MOSFET integrated circuits 202. With such configuration, there is encouraged a distribution of thermal energy to the end that each of a plurality of MOSFET integrated circuits 202 and in one embodiment each MOSFET integrated circuit has approximately a common operating temperature. Configuring driver circuit 20 so that each MOSFET integrated circuit 200 has approximately a common operating temperature reduces noise output by driver circuit 20. Specifically, configuring driver circuit 20 so that each MOSFET integrated circuit 200 has approximately a common operating temperature can be expected to reduce differences in oscillating and switch timing operations that would create ripple and noise in an output of driver circuit 20.

The system in one embodiment is housed in a housing 12 provided by a 4×6×2 in.$^3$ watertight plastic enclosure, No. 073 of the type provided by Serpac, Inc. The housing holds the circuit (1.5×2×1 in.$^3$) and six 9.6V, 1600 mA h NiCad rechargeable battery packs (No. 23-432 available from RadioShack Corporation) tied together in series through two single draw rotary switches.

Referring again to FIG. 1, the various impedances of driver circuit 20, transmission line 70, and transducer 90 can be coordinated in a specific manner. In one embodiment, driver circuit 20 has an output impedance of about 0.5 Ohms. Provisioning driver circuit 20 to have an output impedance that is not matched with the impedance of transducer 90 improves energy transfer efficiency of apparatus 1000. By provisioning driver circuit 20 to have a low output impedance very little energy is dissipated as heat in driver circuit 20. Accordingly, driver circuit 20 will be maintained in a state that is safe to the touch throughout operation of driver circuit 20.

An impedance of transmission line 70 can also be coordinated with the output impedance of driver circuit 20 and an impedance of transducer 90. In one example, transmission line 70 can be provisioned to have an impedance of value that is about the output impedance of driver circuit 20 so that the impedance of transmission line 70 matches the output impedance of driver circuit 10, but, like driver circuit 20, is mismatched with respect to transducer 90.

Figure 26:
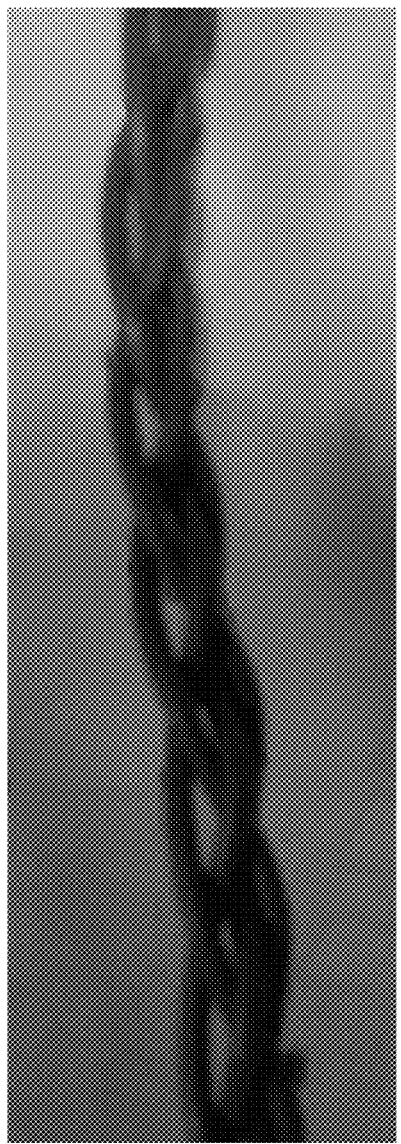
FIG. 26 is a photograph of a transmission line for an ultrasound wave generating apparatus having a braided coaxial cable transmission line.
Figure 27:
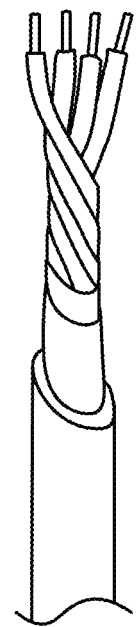
FIG. 27 is a diagram of a transmission line for an ultrasound wave generating apparatus having a twisted coaxial cable transmission line.

In developing apparatus 1000 it was determined that advantages are exhibited by configuring the impedance of transmission line 70 to be low, e.g., about 5 Ohms or lower and in other embodiments, 1 Ohm or lower. In one example, transmission line 70 where provided by a coaxial cable is provided by a 5 Ohm coaxial cable, part number 1/22-15044 available from Cooner Wire, Inc. of Chatsworth, Calif. The impedance of transmission line 70 can be reduced by providing a plurality of coaxial cables in parallel. Where a plurality of coaxial cables are provided in parallel in the formation of transmission line 70, an impedance of transmission line 70 can be expressed as $$R_{EFF} = \frac{Rc}{N}$$

where $R_C$ is the impedance of each individual cable and N is the number of cables. Thus, a transmission line impedance where transmission line 70 includes six (6) of the referenced coaxial cables would be less than 1 Ohm. A plurality of cables can be arranged in a specific configuration. In the embodiment of FIG. 25, transmission line 70 is provided by a plurality of braided coaxial cables arranged in parallel. In the embodiment of FIG. 26, transmission line 70 is provided by a plurality of twisted coaxial cables arranged in parallel. The specific configurations as shown in FIG. 25 and FIG. 26 operate to reduce noise.

[The following section is excerpted from U.S. Provisional Application No. 61/079,712 with minor formatting and editorial changes.]

We have developed a portable high power ultrasound system with a very low output impedance amplifier circuit (less than 0.2 Ohms) that is capable of transferring 95-100% of the energy from the battery supply to the ultrasound transducer. Because little energy is lost in reflection/heat from the mismatch of impedance and the batteries are capable of providing high current, much lower voltages are required to create therapeutic acoustical energy waves. The described system is capable of producing acoustical power outputs over the therapeutic range (greater then 50 watts) from a PZT-4, 1.54 MHz, 0.75 inch diameter piezoelectric ceramic. It is lightweight (under 6 pounds), portable (2×6×4 inches), and powered by a rechargeable battery. The portable therapeutic ultrasound unit has the potential to replace "plug-in" medical systems and RF amplifiers used in research. The system is capable of field service on its internal battery, making it especially useful for military, ambulatory, and remote/field or house-call medical applications.

In the last two decades, therapeutic ultrasound has received attention from the medical community as a tool to relieve arthritis, to improve rehabilitation and to enhance wound healing processes (see J. Wu and W. L. M. Nyborg, "Emerging Therapeutic Ultrasound" Ultrasonics in Medicine, ISBN 978-981-256-685-0 (Print), 2006; G. Aus "Current Status of HIFU and Cryotherapy in Prostate Cancer—A Review"—European Urology, vol. 50 pp. 927-934, 2006; S. Mitragotri "Healing sound: the use of ultrasound in drug delivery and other therapeutic applications"—Nat. Rev. Drug Discovery vol. 4, pp. 255-260, 2005; and M. R. Bailey, V. A. Khokhlova, O. A. Sapozhnikov, S. G. Kargl, and L. A. Crum, "Physical mechanisms of the therapeutic effect of ultrasound: (A review)," Acoust. Phys., vol. 49, no. 4, pp. 369-388, 2003). Ultrasound at higher energies plays a role in surgical applications such as prostate therapy and brain tumor and cardiac tissue ablation, (see M. R. Bailey, V. A. Khokhlova, O. A. Sapozhnikov, S. G. Kargl, and L. A. Crum, "Physical mechanisms of the therapeutic effect of ultrasound: (A review)," Acoust. Phys., vol. 49, no. 4, pp. 369-388, 2003; G. ter Harr and C. Coussios "High Intensity focused ultrasound: Physical principles and devices" International Journal of Hyperthermia, vol. 23, pp. 89-104, 2007; N. I. Vykhodtseva, K. Hynynen, C. Damianou, "Histologic effects of high intensity pulsed ultrasound exposure with subharmonic emission in rabbit brain in vivo", Ultrasound Med. Blol. vol. 21, pp. 969-979, 1995; D. Cesario and et al. "Selection of Ablation Catheters, Energy Sources, and Power Delivery" Contemporary Cardiology, Atrial Fibrillation, pp. 209-221, ISBN: 978-1-58829-856-0 (Print) 978-1-59745-163-5 (Online), 2008.

Therapeutic ultrasound and its effects on tissue properties are currently being studied in research. For example, researchers are assessing the ability of ultrasound for large molecule transdermal drug delivery, in targeted chemotherapy delivery to brain cancer, and in cellular gene transfer applications (see E. J. Park, K. I. Jung, and S. W. Yoon "Acoustic mechanisms as an enhancer for transdermal drug delivery" J. Acoustical Society of America, vol. 107, pp. 2788, 2005; G. K. Lewis, Jr., W. Olbricht, and G. K. Lewis "Acoustic enhanced Evans blue dye perfusion in neurological tissues" Acoustical Society of America, POMA, vol. 2, 2008; C. M. H. Newman and T. Bettinger "Gene therapy progress and prospects: Ultrasound for gene transfer" Gene Therapy, vol. 14, pp. 465-475, 2007. The potential of a combined portable ultrasound imaging and therapeutic systems is currently being studied to great lengths for military and medical applications (see F. L. Lizzi, D. J. Driller, R. H. Silverman, B. Lucas, and A. Rosado, "A therapeutic ultrasound"—S. Vaezy, X, Shi, R. W. Martin, E. Chi, P. I. Nelson, M. R. Bailey, and L. A. Crum, "Real-time visualization of high-intensity focused ultrasound treatment using ultrasound imaging," *Ultrasound Med. Blol., vol.* 27, pp. 32-42, 2001; and L. A. Crum "Smart Therapeutic Ultrasound Device for Mission-Critical Medical Care" Project Report, NASA, 2007. Despite the widespread use of ultrasound, the basic hardware has not changed significantly in the past 50 years (see N. I. Vykhodtseva, K. Hynynen, C. Damianou, "Histologic effects of high intensity pulsed ultrasound exposure with subharmonic emission in rabbit brain in vivo", Ultrasound Med. Blol. Vo. 21, pp. 969-979, 1995; S. Vaezy, X, Shi, R. W. Martin, E. Chi, P. I. Nelson, M. R. Bailey, and L. A. Crum, "Real-time visualization of high-intensity focused ultrasound treatment using ultrasound imaging," Ultrasound Med. Blol., vol. 27, pp. 32-42, 2001; and N. R. Owen, M. R. Bailey, B. J. P. Mortimer, H. Kolve, J. Hossack, and L. A. Crum, "Development of power supplies for portable HIFU therapy systems," in Proc. 3$^{rd}$ Int. Symp. Therapeutic Ultrasound, pp. 1434-1439, 2007. Established methods for ultrasound driving systems, such as high voltage switching and RF amplifiers, often are bulky (20 lbs or more), and can cost more than $20,000. The potential for ultrasound in therapy and research could be greatly enhanced by the development of a cost-effective, portable system for delivering ultrasound.

Commercially available ultrasound drivers and RF amplifiers are generally built with 50 Ohms output impedances that have high voltage amplification/switching of the applied AC signal. The 50 Ohms output impedance often is matched to the transducer using special impedance matching circuitry to enhance power transfer (see N. I. Vykhodtseva, K. Hynynen, C. Damianou, "Histologic effects of high intensity pulsed ultrasound exposure with subharmonic emission in rabbit brain in vivo", Ultrasound Med. Blol. vol. 21, pp. 969-979, 1995; S. Vaezy, X, Shi, R. W. Martin, E. Chi, P. I. Nelson, M. R. Bailey, and L. A. Crum, "Real-time visualization of high-intensity focused ultrasound treatment using ultrasound imaging," *Ultrasound Med. Blol.*, vol. 27, pp. 32-42, 2001; and N. R. Owen, M. R. Bailey, B. J. P. Mortimer, H. Kolve, J. Hossack, and L. A. Crum, "Development of power supplies for portable HIFU therapy systems," in *Proc. 3$^{rd}$ Int. Symp. Therapeutic* Ultrasound, pp. 399-404, 2003). From voltage division, the voltage across the transducer is inversely related to the impedance of the source. Therefore, if the source has a 50 Ohms output impedance and the transducer being driven has a 10 Ohms impedance, only 17% of the energy from the source will be supplied to the transducer. The rest will be reflected or lost in heat. When impedance matching circuitry is used, half of the power from the source is transferred, and the driver becomes more efficient. As described in the this manuscript, we have developed a portable high power ultrasound system with a very low output impedance amplifier circuit (less than 0.2 Ohms) that is capable of transferring 95-100% of the energy from the battery supply to the transducer. Because the output impedance of the drive circuitry is negligible as compared with the ultrasound transducers electrical impedance, little energy is lost in heat. Since the batteries are capable of providing high current, much lower and safer voltages are required to create therapeutic acoustical energy waves. The described system is capable of producing acoustical power outputs over the therapeutic range (greater than 50 watts). It is lightweight (under 6 lbs), portable (2×6×4 inches) and powered by a rechargeable battery. The portable therapeutic ultrasound unit has the potential to replace "plug-in" medical systems and RF amplifiers in research. The system is capable of field service on its internal battery making it especially useful for military, ambulatory, and remote/field to house-call medical applications.

We present the schematic of the low impedance ultrasound driver for the portable therapeutic ultrasound system. We then explain how we incorporate the driving circuitry into the complete system, along with development of the ultrasound probe for the device. We conclude by explaining the measurements conducted to determine the power of the device. We conclude by explaining the measurements conducted to determine the power of the device, acoustical driving efficiency, portability, and system robustness.

Figure 28:
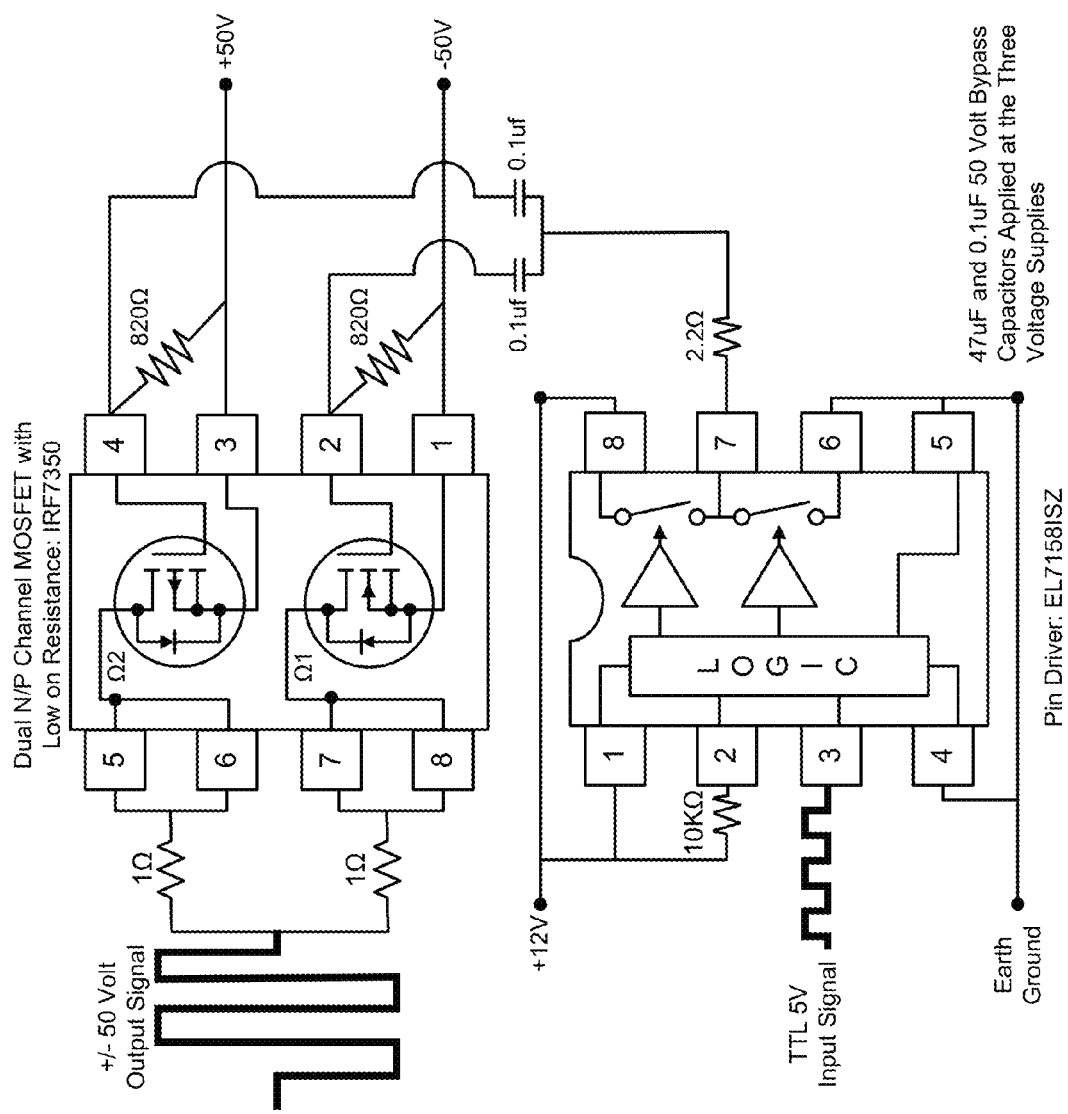
FIG. 28 is a schematic diagram of a driver circuit in combination with a timing circuit.

The circuit layout for the low-output-impedance driver is shown in FIG. 28. A pin driver (EL71581SZ, Intersil Inc.) that is capable of driving high capacitive loads is supplied with a 5 volt square wave transistor-transistor logic (TTL) input at pin 3. The input timing signal came from a 1.54 MHz crystal oscillator (SE1216-ND, Epson Toyocom Inc.) that fit the developed ultrasound probes resonant frequency. Pins 1 and 8 are held at +12 volts with 47 µF and 0.1 µF bypass capacitors to ground. Pin 2 is connected to pin 1 with a 10 k Ω resistor. Pins 4-6 are connected to earth ground. Pin 7 of the pin driver is the output that provides a 12 volt square wave that regulates the switching of the MOSFET's voltage drain. From pin 7 of the pin driver a 2.2 Ohms resistor splits off with two 0.1 µF capacitors into the input pins 2 and 4 of the low on resistance N/P channel MOSFET (IRF7350, International Rectifier, Inc.). Pins 1 and 3 of the MOSFET are held at a maximum of −/+50 volts respectively with 820 Ohms resistors across pins 1-2 and 3-4 as shown. 47 µF and 0.1 µF bypass capacitors to ground are applied as well to pins 1 and 3 of the MOSFET. Pins 5-6 and 7-8 of the MOSFET are tied together and coupled through 1 Ohm, 5 watt power resistors with the output drive signal applied to the ultrasound transducer.

Figure 29:
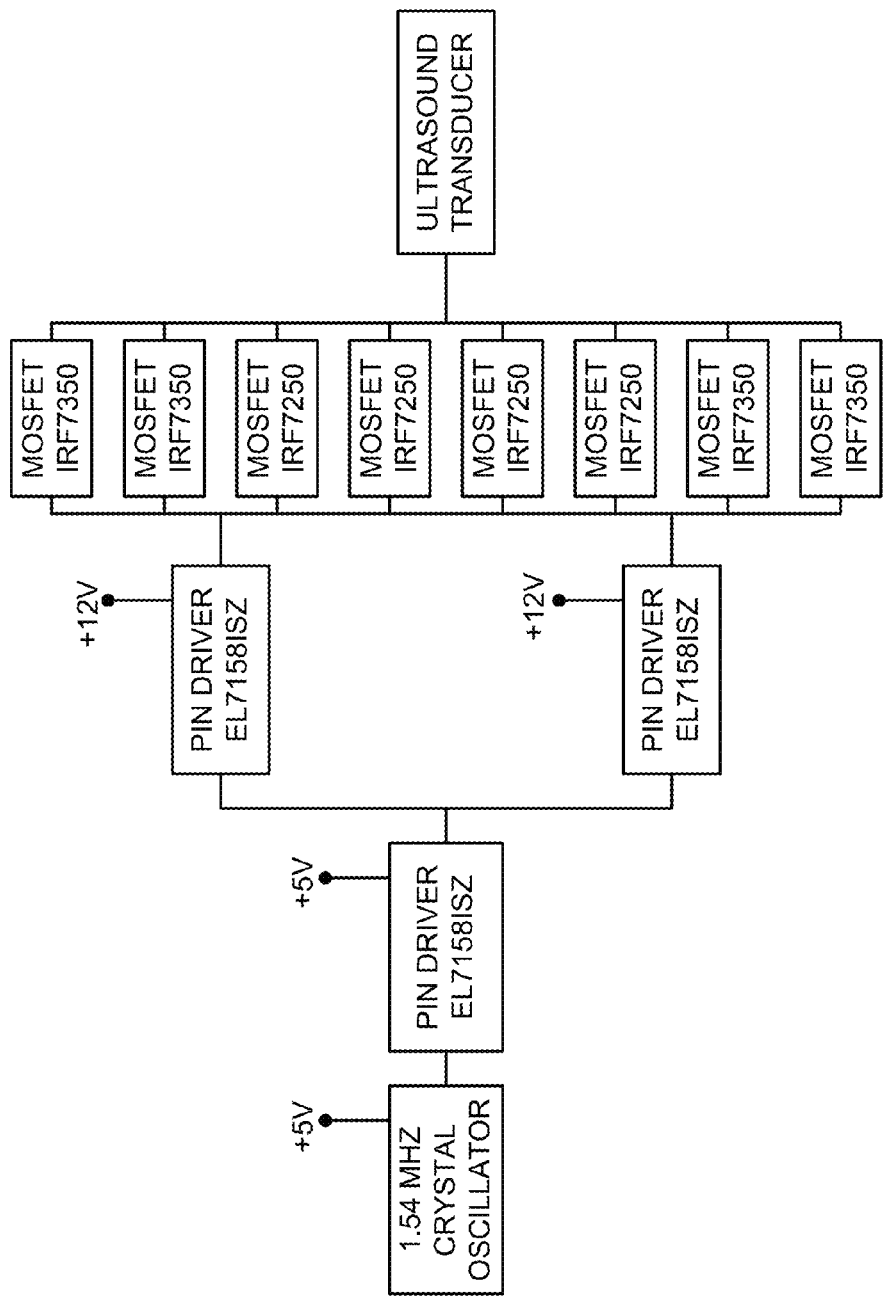
FIG. 29 is a block diagram of a power supply having a driver circuit with a plurality of transistor pairs arranged in parallel.

The Intersil Inc. EL71581SZ pin driver acts as the logic switch for the MOSFETs that supply the power oscillation drive to the ultrasound transducer. For our high power application that requires high current, pin drivers are used to switch MOSFETs in parallel to lower the current burden on each MOSFET. As shown in FIG. 29, a single timed pin driver at 5 volts drives two pin drivers at 12 volts as a branching cascade to switch four MOSFETs each for the high power ultrasound driving system. Each pin driver/MOSFET unit is wired as shown in FIG. 28. The output impedance of the driver was determined from manufacturer values of the MOSFETs, and measured resistance values to be approximately 0.2 Ohms.

Regarding FIG. 28, FIG. 28 shows circuit schematic of the low output impedance ultrasound driver. Shown in FIG. 28, a pin driver is appropriately timed with a TTL 5 volt signal form a 1.54 MHz crystal oscillator that switches the drain of the low output impedance MOSFET from +/−50 volts maximum.

Referring to FIG. 29, FIG. 29 shows a driving circuit used in portable ultrasound system. The working unit of FIG. 28 may be applied in parallel stages to reduce the power/heat dissipation in each MOSFET to allow for high current driving to the transducer.

A parts list for amplifier components is summarized in Table AA.

TABLE AA

1. Pin driver, quantity 3 (#EL7158ISZ, Intersil Inc.)
2. 1.54 MHz TTL Crystal Oscillator, quantity 1 (#SE1216- ND, Epson Toyocom Inc.)
3. 10k Ohms, +/−5%, ¼ watt resistor, quantity 3 (General)
4. 820 Ohms, +/−5%, ¼ watt resistor, quantity 16 (General)
5. 2.2 Ohms, +/−5%, ¼ watt resistor, quantity 8 (General)
6. 1 Ohm, +/−5%, 5 watt resistor, quantity 8 (General)
7. 47 uF, +/−20%, 50 volt electrolytic capacitor, quantity 12 (General)
8. 0.1 uF, +/−20%, 50 volt electrolytic capacitor, quantity 12 (General)

A parts list for the housing and other components is summarized in Table BB:

TABLE BB

1. Plastic enclosure, quantity 1 (#073, Serpac Inc.)
2. Rotary switch, quantity 2 (#275-1386, RadioShack Corporation)
3. SPST 3-way switch, quantity 1 (#275-612, RadioShack Corporation)
4. LED, quantity 1 (#276-316, RadioShack Corporation)
5. Voltage regulator 5 volts, quantity 1 (#276-1770, RadioShack Corporation)
6. Voltage regulator 12 volts, quantity 2 (#276-1771, RadioShack Corporation)
7. Prototyping board, quantity 1 (#276-150, RadioShack Corporation)
8. DC power connector, quantity 1 (#274-1563, RadioShack Corporation)
9. NiCad 9.6 volt battery with charger, quantity 6 (#23-432, RadioShack Corporation)

Referring to a system design layout, the completed system shown in Figures CC and DD is housed in a 4×6×2 inch watertight plastic enclosure (#073, Serpac Inc.). Along with the circuit (1.5×2×1 inches in size), the housing holds six 10 volt 1600 mAh NiCad rechargeable battery packs (#23-432, RadioShack Corporation) tied together through two single draw rotary switches that allow the user to adjust power delivery to the transducer through the MOSFETs in 10 volt increments, providing a maximum of +/−30 volts. A blue "on" LED is tied into the on/off switch that supplies power to the crystal oscillator and pin driver through 5V and 12V 1 amp voltage regulators. The output of the device is terminated in a male BNC connector on the front panel. A battery recharge port is located at the back of the system.

Figure 30:
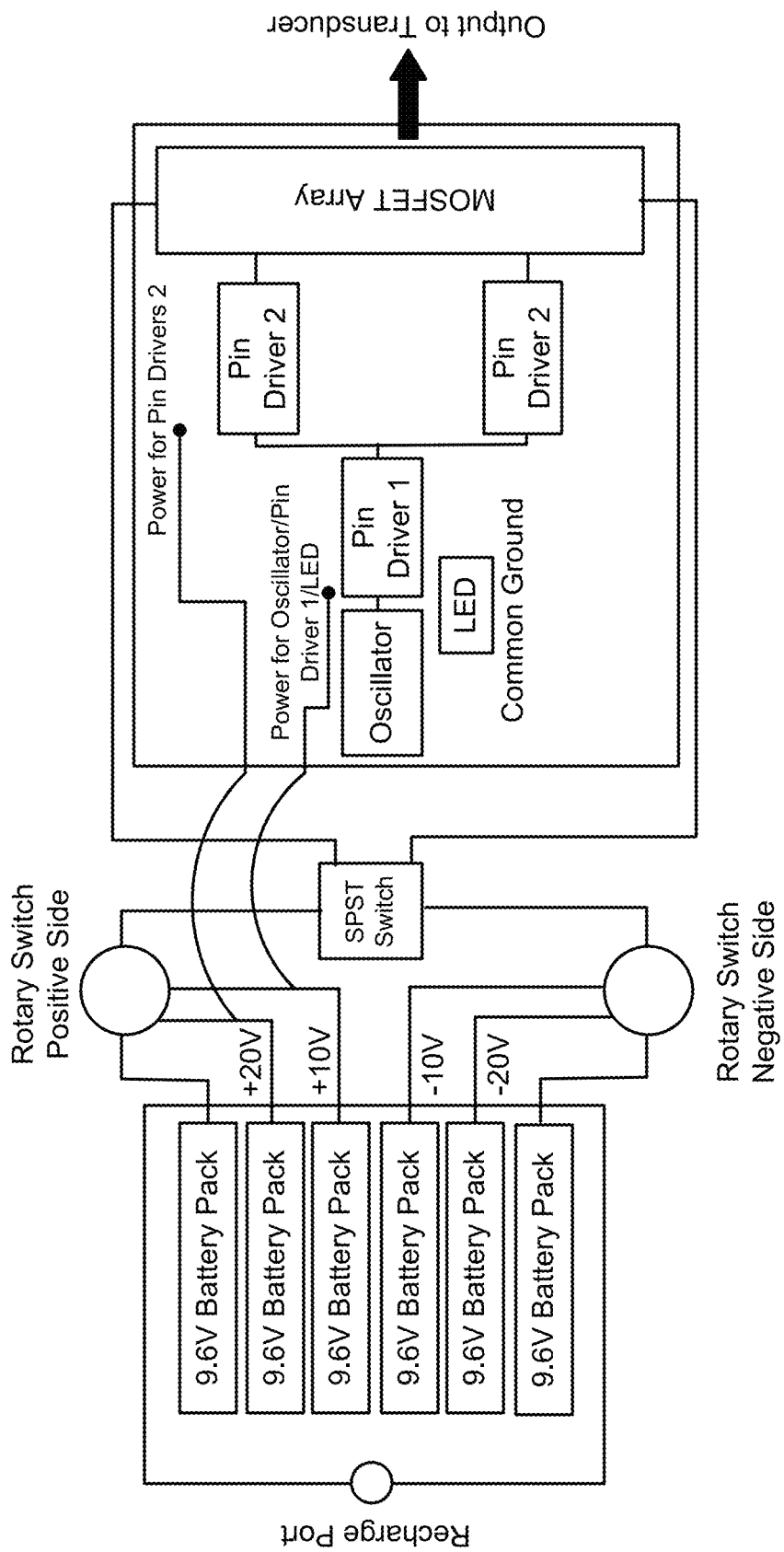
FIG. 30 is a schematic diagram of a power supply having a driver circuit with a plurality of transistor pairs arranged in parallel.

Referring to FIG. 30, FIG. 30 shows a wire layout for a portable ultrasound system.

Figure 31:
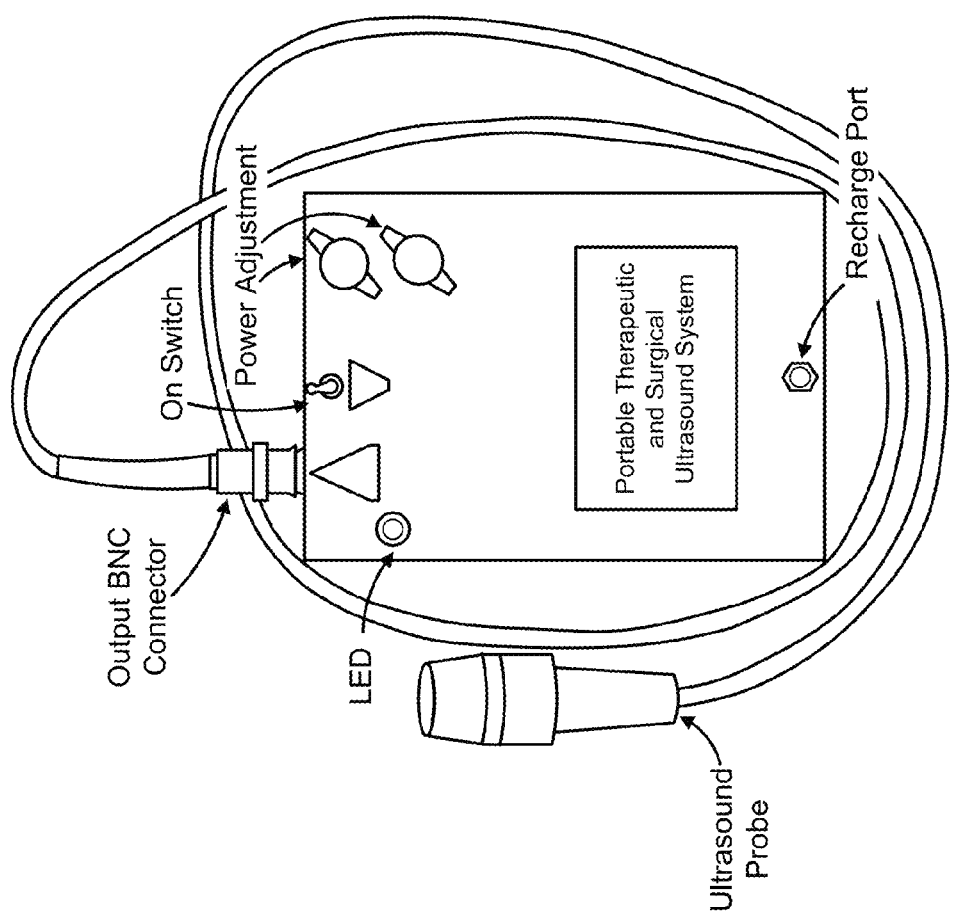
FIG. 31 is a physical form view of an ultrasound wave generating apparatus.

Referring to FIG. 31, FIG. 31 shows a Portable therapeutic ultrasound system with 1.54 MHz ultrasonic probe, 4×6×2° inches in size and weighs 5.5 lbs.

Referring to the described ultrasonic probe design, the ultrasound probe is constructed from lead zirconate titanate (PZT-4), 1.54 MHz, 0.75 in diameter piezoelectric ceramic with a radius of curvature corresponding to 1.5 in (EBL Products Inc.). The ceramic (air-backed) is housed in a PVC ergonomic plastic assembly. The clear acrylic front of the transducer acts as a protective cover to the ceramic and an in-plane focal alignment standoff for the ultrasound energy produced FIG. 31. The probe is wired with 22 gauge coaxial cable terminated with a female BNC connector. The electrical impedance of the ultrasound probe was measured using commonly known methods (see FIG. 32) to determine the resonant frequency for high power driving efficiency (see J. S. Bottman "Pulse-based impedance measurement instrument" U.S. Pat. No. 5,633,801, 1997).

Figure 33:
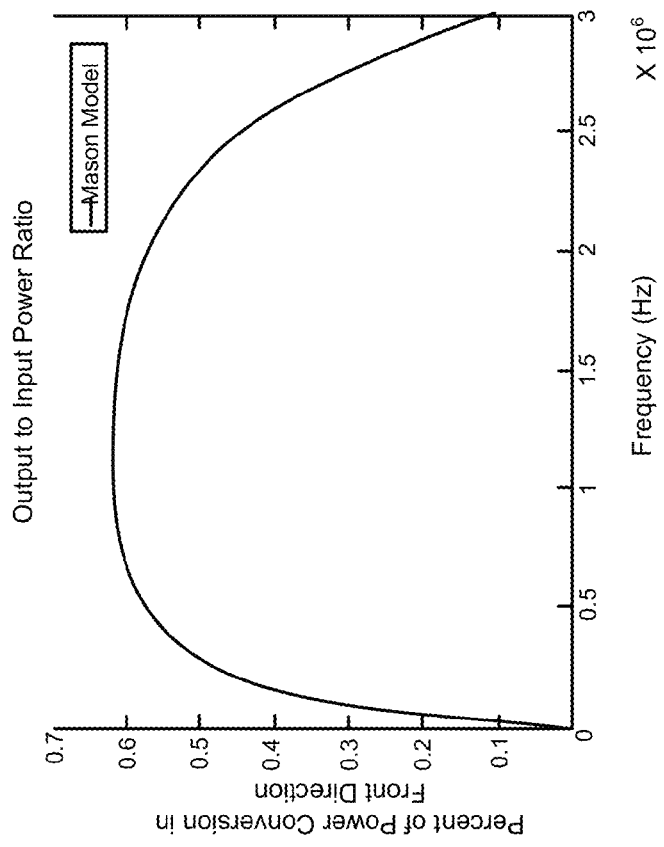
FIG. 33 is an output power efficiency curve illustrating a percent of power conversion for an ultrasound wave generating apparatus over a range of frequencies.
Figure 32:
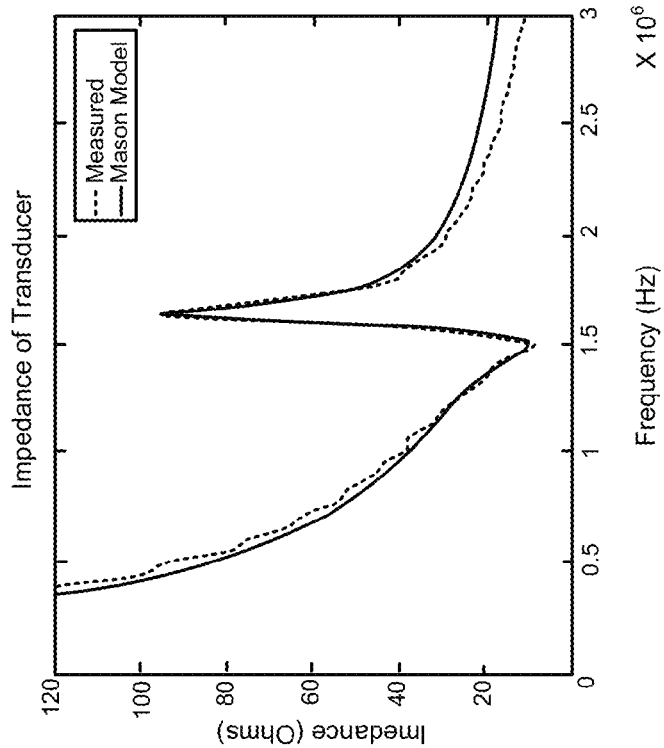
FIG. 32 is an impedance curve illustrating impedance of an exemplary transducer.

Referring to FIG. 32, FIG. 32 shows an impedance plot measured and modeled using Mason Model of transmission lines. Referring to FIG. 33, FIG. 33 shows a plot of calculated acoustic conversion efficiency from the Mason Model.

Example 1

A variety of tests were performed using the system for purposes of performing system measurements and characterization. First the ultrasonic power was determined with a force balance technique where we measured the force the ultrasound exerted on an acoustic absorbing object (see S. Maruvada, G. R. Harris, and B. A. Herman "Acoustic power calibration of high-intensity focused ultrasound transducers using a radiation force technique" J. Acoustical Society of America, vol. 121, pp. 1434-1439, 2007). We compared these results to electrical measurements of power, using the electrical properties of the probe and experimentally measured ultrasonic power conversion efficiency (see M. Redwood and J. Lamb "On the Measurement of Attenuation and Ultrasonic Delay Lines." Proceedings of the IEEE, vol. 103, pp. 773-780, 1956). Second, the battery life was determined for various output powers under one charge. Third, we tested the device with other 1.7 MHz-7 MHz ultrasonic probes by interchanging the 1.54 MHz crystal oscillator with a function generator and running with 1.7, 2.2, and 7.5 MHz transducers off of the system.

The electrical impedance of 12 Ohms and an acoustic conversion efficiency of 63% at 1.54 MHz were obtained from the characteristics of the ultrasound probe shown in FIG. 31 and used to determine power from the voltage measurement across the transducer. The ultrasonic power was measured at each power setting and complied in Table CC. The force balance approach gave slightly higher acoustic power readings compared with the electrical power measurements. The battery life at each power setting for sustained power output is also tabulated in Table CC. Maximal system life was for 1.7 hrs at 5-6 watts of acoustic energy. At the maximum acoustic energy setting battery life dropped to 0.7 hrs.

TABLE CC

Complied Acoustic Power Measurements And Battery Life

| Voltage Setting Vpp-Vpp (volts) | 20 | 30 | 40 | 50 | 60 |
|---|---|---|---|---|---|
| Force Balance (watts) | 6.28 | 10.5 | 23.5 | 43.4 | 55.8 |
| Electrical Measurement (watts) | 5.25 | 11.8 | 21.0 | 32.8 | 47.3 |
| Power Average (watts) | 5.77 | 11.5 | 22.5 | 38.1 | 51.4 |
| System Battery Life (hours) | 1.7 | 1.2 | 1.0 | 0.8 | 0.7 |

The device maintained good working condition after sustaining an accidental 4 foot drop test with only a slight fracture to the corner of the housing. Ease of use was ascertained by having students connect to ultrasound probe to the device, use the device to cause water levitation and cavitation as shown is FIGS. 32 and 33, and recharge the system for another use (eight hour recharge time overnight).

Figure 34:
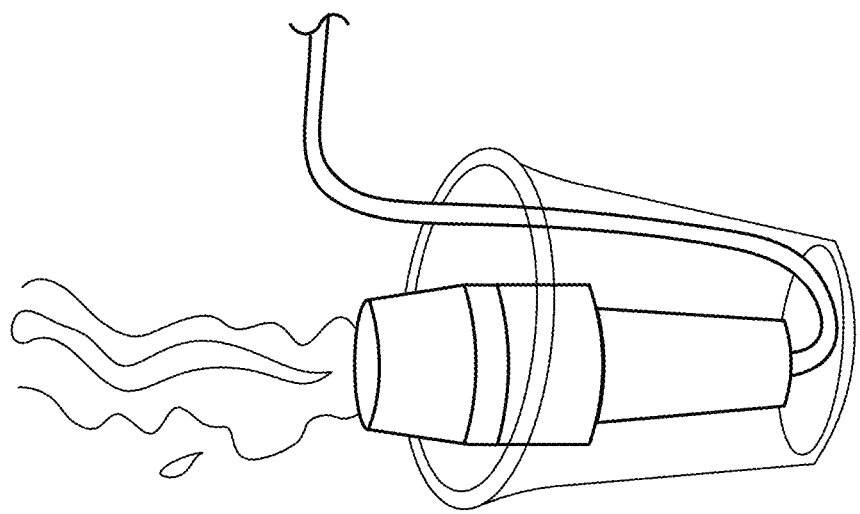
FIG. 34 is a photograph illustrating a probe in one embodiment.

Referring to FIG. 34, FIG. 34 shows an ultrasound transducer levitating and cavitating water at full system power.

The portability of the system compares well with that of commercially available therapeutic systems. Clinical therapeutic systems such as the THERASOUND medical instrumentation line from RichMar Inc. provide a maximum of 4 watts of acoustical energy to the patient. These systems are slightly larger (7×7×6 inches), similarly heavy (5-6 lbs), and require AC power. Since most of the mass of our system is batteries, for low power applications such as the THERA-SOUND, the housing of our device could be made much smaller, similar to the size of a cellular phone. For high power applications such as HIFU used in ultrasound surgery, our system is substantially smaller and lighter than typical RF amplifiers (usually 12×24×7 inches and 20 lbs). Since most surgical ultrasound is used in the 40-60 watt range, the portable system satisfies current requirements. In research applications, higher power ultrasonics are being studied that require more energy than our current system can provide on battery supply/The circuitry in the device, according to the data sheet provided from International Rectifier, Inc. can provide 100 volts peak to peak. At this voltage level, our acoustic efficiency model estimates it can produce an ultrasonic power of over 130 watts.

Adaptability of the circuitry for other ultrasonic transducers was found to be straightforward. The function generator in place of the crystal oscillator drove 1.7, 2.2, and 7.5 MHz, PZT-4 focused transducers at noticeable cavitation powers when submerged in degassed water. With the 7.5 MHz transducer, the MOSFETs began to heat to damage after 2 minutes when full power was continuously supplied. This was from the probe's low electrical impedance (4 Ohms) and a very high current draw of 7.5 amps. For continuous operation for the 7.5 MHz probe, it would be advantageous to parallel more MOSFETs or use heat sinks to reduce heating.

End of Example 1

Implementation of the low output impedance amplifier is straight forward and provides highly efficient ultrasound driving. From manufacturer's specifications of the electrical components and general testing of the system, it is operable form the 1-10 MHz which is ideal for medical therapeutic ultrasound and HIFU systems. In selecting the array of MOSFETs (how many are required) to meet the power requirements for ultrasound driving, it may be assumed that the output of the impedance is very low (mmOhm's). A simple Ohm's Law calculation of the current required using the electrical impedance of the transducer, and the voltage supply of the MOSFETs drain is a good starting point to determine current requirements.

The portable therapeutic ultrasound system is based on driving an ultrasound transducer with a very low output impedance AC source, so that power from the supply is efficiently transferred to the device. Our ultrasound driving circuit has an output impedance of 0.2 Ohms and provides switching of +/−30 volts (capable of +/−50 volts). The device can provide over 50 watts of acoustic energy from the 1.54 MHz transducer. Because the device consists of multiple battery packs, voltage regulators were wired to the nearest battery level to reduce energy waste. Combining the LED on light, the heating of MOSFETs, voltage regulators and resistors, along with a back calculation of the acoustic output energy measured, we calculated an energy waste of approximately 1-5%. Compared with commercially available systems, the device is much smaller, lighter, and costs only $150.00 ($120.00 of which was for rechargeable battery packs) which allows higher power ultrasound to be easily accessible.

[End of excerpted section based on U.S. Provisional Application No. 61/079,712 with minor formatting and editorial changes.]

A small sample of systems methods and apparatus that are described herein is as follows:

A1. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency.

A2. The ultrasound wave generating apparatus of claim A1, wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is a continuous bipolar drive signal so that both of compression forces and expansion forces are imparted to the ultrasound transducer.

A3. The ultrasound wave generating apparatus of claim A1, wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is an imbalanced continuous bipolar drive signal so that both of compression forces and expansion forces are imparted to the ultrasound transducer, and further so that the compression forces are of greater magnitude than the expansion forces.

A4. The ultrasound wave generating apparatus of claim A1, wherein the driver circuit is operative so that the drive signal has an output current capacity of greater than 50 amperes.

A5. The ultrasound wave generating apparatus of claim A1, wherein the power supply includes a capacitive coupling circuit coupling the timing signal to the first and second gates of the transistor pair, wherein the timing signal is a unipolar timing signal, and wherein the capacitive coupling circuit converts the unipolar timing signal into a bipolar input signal for input into the driver circuit.

A6. The ultrasound wave generating apparatus of claim A1, wherein the transistor based driver circuit includes a plurality of transistor pairs connected in parallel, each of the transistor pairs having first and second transistors, wherein each of the transistor pairs is coupled to the first and second clamping voltage terminals.

A7. The ultrasound wave generating apparatus of claim A1, wherein the ultrasound wave generating apparatus includes a user interface and is operative so that at least one characteristic of the drive signal can be changed in response to an operator control input that is input utilizing the user interface.

A8. The ultrasound wave generating apparatus of claim A1, wherein the ultrasound wave generating apparatus is adapted so that the ultrasound transducer is incorporated in a replaceable ultrasound transducer assembly that is one of a plurality of candidate ultrasound transducer assemblies that can be associated to the ultrasound wave generating apparatus, and wherein the ultrasound wave generating apparatus is operative so that the drive signal has at least one characteristic that is responsive to which of the plurality of candidate ultrasound transducer assemblies is presently associated to the ultrasound wave generating apparatus.

A9. The ultrasound wave generating apparatus of claim A1, wherein the ultrasound wave generating apparatus includes a user interface and is adapted so that the ultrasound transducer is incorporated in a replaceable ultrasound transducer assembly that is one of a plurality of candidate ultrasound transducer assemblies that can be associated to the ultrasound wave generating apparatus, wherein the ultrasound wave generating apparatus is operative so that the drive signal output by the driver circuit is responsive to each of (a) a switching of a candidate transducer assembly, and (b) a control input that is input by an operator utilizing the user interface.

A10. The ultrasound wave generating apparatus of claim A9, wherein each of the plurality of candidate transducer assemblies includes a timing device disposed therein for controlling a timing of the driver circuit.

A11. The ultrasound wave generating apparatus of claim A1, wherein the ultrasound wave generating apparatus is operative in a first mode of operation and in a second mode of operation, wherein the ultrasound wave generating apparatus in the first mode of operation outputs an imbalanced bipolar output drive signal, wherein the apparatus in the second mode of operation outputs an output drive signal that is selected from the group consisting of a unipolar output drive signal and a balanced output drive signal.

A12. The ultrasound wave generating apparatus of claim A11, wherein the ultrasound wave generating apparatus includes a replaceable transducer assembly incorporating the transducer, the transducer assembly being one of a plurality of candidate transducer assemblies, wherein the ultrasound wave generating apparatus is operative so that the ultrasound wave generating apparatus switches operation from the first mode of operation to the second mode of operation responsively to the transducer assembly being replaced with another of the plurality of candidate transducer assemblies.

A13. The ultrasound wave generating apparatus of claim A1, wherein the apparatus further includes a housing for housing the ultrasound transducer, the housing having a distal end at which the ultrasound transducer is disposed, wherein there is further disposed at the distal end a standoff component defining a cavity for carrying ultrasound coupling medium, the standoff component having a light transmissive wall adapted to permit visual viewing of an interior of the cavity through the light transmissive wall.

A14. The ultrasound wave generating apparatus of claim A1, wherein the apparatus includes a transmission line coupling the driver circuit and the transducer, the transmission line including a plurality of coaxial cables arranged in parallel, and further being arranged in a braid configuration.

A15. The ultrasound wave generating apparatus of claim A1, wherein the apparatus includes a transmission line coupling the driver circuit and the transducer, the transmission line including a plurality of coaxial cables arranged in parallel, and further being arranged in a twisted configuration.

A16. The ultrasound wave generating apparatus of claim A1, wherein the transducer comprises a single transducer element having a first associated nominal frequency of resonance.

A17. The ultrasound wave generating apparatus of claim A1, wherein the transducer comprises a plurality of transducer elements.

A18. The ultrasound wave generating apparatus of claim A1, wherein the transducer comprises first and second transducer elements, the first transducer element having a first resonant frequency, the second transducer element having a second resonant frequency.

A19. The ultrasound wave generating apparatus of claim A1, wherein the ultrasound transducer comprises first and second transducer elements, the first transducer element having a first resonant frequency, the second transducer element having a second resonant frequency, and wherein the apparatus is configured so that the driver circuit is operative to output a frequency sweeping drive signal, the frequency sweeping drive signal having a frequency corresponding to the first resonant frequency during a first period, the frequency sweeping drive signal having a frequency corresponding to the second resonant frequency during a second period.

A20. The ultrasound wave generating apparatus of claim A1, wherein the power supply has a plurality of power supply stages, each power supply stage having an associated driver circuit and power source, wherein the plurality of the power supply stages include first and second power supply stages, the second power supply stage being successive in relation to the first power supply stage, and wherein an output of the first of the power supply stages is input into a stage ground of the second power supply stage.

A21. The ultrasound wave generating apparatus of claim A1, wherein the power supply includes a user interface configured to permit an operator to independently adjust the first terminal clamping voltage and the second terminal clamping voltage via input of control inputs utilizing the user interface.

A22. The ultrasound wave generating apparatus of claim A1, wherein the power source includes a battery power source.

A23. The ultrasound wave generating apparatus of claim A1, wherein the power source includes an AC/DC converter.

A24. The ultrasound wave generating apparatus of claim A1, wherein the driver circuit includes a MOSFET integrated circuit, and wherein the apparatus includes a housing and printed circuit board for carrying the MOSFET integrated circuit, the printed circuit having a peripheral edge that is proximate the housing when the printed circuit board is disposed in the housing, wherein the MOSFET integrated circuit is disposed on the printed circuit at a location that is more proximate the peripheral edge of the circuit board that a longitudinal centerline of the printed circuit board.

A25. The ultrasound wave generating apparatus of claim A1, wherein the driver circuit includes a plurality of transistor pairs and a plurality of pin drivers for providing switching of the plurality of transistor pairs, wherein the driver circuit is configured so that each of the plurality of pin drivers for providing switching drives a common number of transistor pairs.

A26. The ultrasound wave generating apparatus of claim A1, wherein the apparatus includes a printed circuit board carrying the first and second transistors of the driver circuit and wherein an output of the driver circuit includes common node that combines outputs of the first and second transistors, wherein the common output node is constituted by an output voltage plane having a planar surface area partially defining a surface of the printed circuit board.

B1. An ultrasound wave generating apparatus comprising:

a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;

a hand held housing for housing the power supply;

an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;

wherein the driver circuit is operative to output a drive signal having a frequency corresponding to the resonant frequency; and wherein the apparatus is configured so that the transducer has an associated load voltage when the driver circuit outputs the drive signal to drive the transducer at a frequency corresponding to the resonant frequency, wherein the apparatus is further configured so that driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;

wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is an imbalanced continuous bipolar drive signal so that both of compression forces and expansion forces are imparted to the ultrasound transducer, and further so that the compression forces are of greater magnitude than the expansion forces;

wherein the driver circuit is operative so that the drive signal has an output current capacity of greater than 50 amperes.

wherein the power supply includes a capacitive coupling circuit coupling the timing signal to the first and second gates of the transistor pair, wherein the timing signal is a unipolar timing signal, and wherein the capacitive coupling circuit converts the unipolar timing signal into a bipolar input signal for input into the driver circuit;

wherein the transistor based driver circuit includes a plurality of transistor pairs connected in parallel, each of the transistor pairs having first and second transistors, wherein each of the transistor pairs is coupled to the first and second clamping voltage terminals;

wherein the ultrasound wave generating apparatus includes a user interface and is adapted so that the ultrasound transducer is incorporated in a replaceable ultrasound transducer assembly that is one of a plurality of candidate, ultrasound transducer assemblies that can be associated to the ultrasound wave generating apparatus, wherein the ultrasound wave generating apparatus is operative so that the drive signal output by the driver circuit is responsive to each of (a) a switching of a candidate transducer assembly, and (b) a control input that is input by an operator utilizing the user interface;

wherein the apparatus further includes a housing for housing the ultrasound transducer, the housing having a distal end at which the ultrasound transducer is disposed, wherein there is further disposed at the distal end a standoff component defining a cavity for carrying ultrasound coupling medium, the standoff component having a light transmissive wall adapted to permit visual viewing of an interior of the cavity through the light transmissive wall;

wherein the apparatus includes a transmission line coupling the driver circuit and the transducer, the transmission line including a plurality of coaxial cables arranged in parallel, and further being arranged in one of a braid or twisted configuration;

wherein the power supply has a plurality of power supply stages, each power supply stage having an associated driver circuit and power source, wherein the plurality of the power supply stages include first and second power supply stages, the second power supply stage being successive in relation to the first power supply stage, and wherein an output of the first of the power supply stages is input into a stage ground of the second power supply stage.

wherein the user interface is configured to permit an operator to independently adjust the first terminal clamping voltage and the second terminal clamping voltage via input of control inputs utilizing the user interface;

wherein the power source includes a battery power source;

wherein the driver circuit includes a MOSFET integrated circuit, and wherein the apparatus includes a housing and printed circuit board for carrying the MOSFET integrated circuit, the printed circuit having a peripheral edge that is proximate the housing when the printed circuit board is disposed in the housing, wherein the MOSFET integrated circuit is disposed on the printed circuit at a location that is more proximate the peripheral edge of the circuit board that a longitudinal centerline of the printed circuit board;

wherein the driver circuit includes a plurality of transistor pairs and a plurality of pin drivers for providing switching of the plurality of transistor pairs, wherein the driver circuit is configured so that each of the plurality of pin drivers for providing switching drives a common number of transistor pairs; and wherein the apparatus includes a printed circuit board carrying the first and second transistors of the driver circuit and wherein an output of the driver circuit includes common node that combines outputs of the first and second transistors, wherein the common output node is constituted by an output voltage plane having a planar surface area partially defining a surface of the printed circuit board.

C1. An ultrasound wave generating apparatus comprising:

a power supply having a timing circuit for outputting a timing signal, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;

an ultrasound transducer configured to emit ultrasound energy, the ultrasound transducer being coupled to the driver circuit so that the drive signal output by the driver circuit drives the ultrasound transducer, wherein the ultrasound transducer includes an impedance rating and a frequency rating and wherein the driver circuit is operative to output the drive signal at a frequency of about the frequency rating of the ultrasound transducer; and wherein the driver circuit includes an output impedance and wherein the apparatus is configured so a value of the output impedance of the driver circuit is less than 10 percent of a value of the impedance rating of the ultrasound transducer.

C2. The ultrasound wave generating apparatus of claim C1, wherein the ultrasound wave generating apparatus is operative to output more than 50 Watts of ultrasound energy.

C3. The ultrasound wave generating apparatus of claim C1, wherein the power supply includes a capacitive coupling circuit coupling the timing signal to the first and second gates of the transistor pair, wherein the timing signal is a unipolar timing signal, and wherein the capacitive coupling circuit converts the unipolar timing signal into a bipolar input signal for input into the driver circuit.

C4. The ultrasound wave generating apparatus of claim C1, wherein the transistor based driver circuit includes a plurality of transistor pairs connected in parallel, each of the transistor pairs having first and second transistors, wherein each of the transistor pairs is coupled to the first and second clamping voltage terminals.

C5. The ultrasound wave generating apparatus of claim C1, wherein the apparatus includes a battery power source.

C6. The ultrasound wave generating apparatus of claim C1, wherein the power supply includes a user interface configured to permit an operator to independently adjust the first terminal clamping voltage and the second terminal clamping voltage via input of control inputs utilizing the user interface.

D1. An ultrasound wave generating apparatus comprising:

a power supply having a timing circuit for outputting a timing signal, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;

an ultrasound transducer configured to emit ultrasound energy, the ultrasound transducer being coupled to the driver circuit so that the drive signal output by the driver circuit drives the ultrasound transducer, wherein the ultrasound transducer includes an impedance rating and a frequency rating and wherein the driver circuit is operative to output the drive signal at a frequency of about the frequency rating of the ultrasound transducer;

wherein the driver circuit includes an output impedance and wherein the apparatus is configured so a value of the output impedance of the driver circuit is less than 10 percent of a value of the impedance rating of the ultrasound transducer;

wherein the ultrasound wave generating apparatus is operative to output more than 50 Watts of ultrasound energy;

wherein the power supply includes a capacitive coupling circuit coupling the timing signal to the first and second gates of the transistor pair, wherein the timing signal is a unipolar timing signal, and wherein the capacitive coupling circuit converts the unipolar timing signal into a bipolar input signal for input into the driver circuit;

wherein the transistor based driver circuit includes a plurality of transistor pairs connected in parallel, each of the transistor pairs having first and second transistors, wherein each of the transistor pairs is coupled to the first and second clamping voltage terminals;

wherein the apparatus includes a battery power source; and wherein the power supply includes a user interface configured to permit an operator to independently adjust the first terminal clamping voltage and the second terminal clamping voltage via input of control inputs utilizing the user interface.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than the mentioned certain number of elements.

The invention claimed is:

1. An ultrasound wave generating apparatus comprising:
a power supply having a power source, a timing circuit, and a transistor based driver circuit for output of a drive signal for driving an ultrasound transducer, wherein the ultrasound transducer is an ultrasound transducer selected from the group consisting of (a) a single element ultrasound transducer having a single transducer element, (b) a multiple element ultrasound transducer having three or fewer transducer elements, and (c) a multiple element ultrasound transducer having a plurality of transducer elements arranged in layers, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;

the ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;

wherein the driver circuit is operative to output a drive signal having a frequency corresponding to the resonant frequency; and wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency.

2. The ultrasound wave generating apparatus of claim 1, wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is a continuous bipolar drive signal so that both of compression forces and expansion forces are imparted to the ultrasound transducer.

3. The ultrasound wave generating apparatus of claim 1, wherein the driver circuit is operative so that the drive signal has an output current capacity of greater than 50 amperes.

4. The ultrasound wave generating apparatus of claim 1, wherein the power supply includes a capacitive coupling circuit coupling the timing signal to the first and second gates of the transistor pair, wherein the timing signal is a unipolar timing signal, and wherein the capacitive coupling circuit converts the unipolar timing signal into a bipolar input signal for input into the driver circuit.

5. The ultrasound wave generating apparatus of claim 1, wherein the ultrasound wave generating apparatus includes a user interface and is operative so that at least one characteristic of the drive signal can be changed in response to an operator control input that is input utilizing the user interface.

6. The ultrasound wave generating apparatus of claim 1, wherein the apparatus further includes a housing for housing the ultrasound transducer, the housing having a distal end at which the ultrasound transducer is disposed, wherein there is further disposed at the distal end a standoff component defining a cavity for carrying ultrasound coupling medium, the standoff component having a light transmissive wall adapted to permit visual viewing of an interior of the cavity through the light transmissive wall.

7. The ultrasound wave generating apparatus of claim 1, wherein the apparatus includes a transmission line coupling the driver circuit and the transducer, the transmission line including a plurality of coaxial cables arranged in parallel, and further being arranged in a braid configuration.

8. The ultrasound wave generating apparatus of claim 1, wherein the apparatus includes a transmission line coupling the driver circuit and the transducer, the transmission line including a plurality of coaxial cables arranged in parallel, and further being arranged in a twisted configuration.

9. The ultrasound wave generating apparatus of claim 1, wherein the transducer comprises a single transducer element having a first associated nominal frequency of resonance.

10. The ultrasound wave generating apparatus of claim 1, wherein the transducer comprises a plurality of transducer elements.

11. The ultrasound wave generating apparatus of claim 1, wherein the power source includes a battery power source.

12. The ultrasound wave generating apparatus of claim 1, wherein the power source includes an AC/DC converter.

13. The ultrasound wave generating apparatus of claim 1, wherein the driver circuit includes a MOSFET integrated circuit, and wherein the apparatus includes a housing and printed circuit board for carrying the MOSFET integrated circuit, the printed circuit having a peripheral edge that is proximate the housing when the printed circuit board is disposed in the housing, wherein the MOSFET integrated circuit is disposed on the printed circuit at a location that is more proximate the peripheral edge of the circuit board that a longitudinal centerline of the printed circuit board.

14. The ultrasound wave generating apparatus of claim 1, wherein the driver circuit includes a plurality of transistor pairs and a plurality of integrated circuits for providing switching of the plurality of transistor pairs, wherein the driver circuit is configured so that each of the plurality of integrated circuits for providing switching drives a common number of transistor pairs.

15. The ultrasound wave generating apparatus of claim 1, wherein the apparatus includes a printed circuit board carrying the first and second transistors of the driver circuit and wherein an output of the driver circuit includes common node that combines outputs of the first and second transistors, wherein the common node is constituted by an output voltage plane having a planar surface area partially defining a surface of the printed circuit board.

16. The ultrasound wave generating apparatus of claim 1, wherein the ultrasound wave generating apparatus includes a probe having a housing in which the ultrasound transducer is disposed, the probe housing receiving an ultrasound coupling medium.

17. The ultrasound wave generating apparatus of claim 1, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

18. The ultrasound wave generating apparatus of claim 1, wherein the power source includes a battery power source, wherein the ultrasound wave generating apparatus includes a housing capable of being held in a hand, and wherein the battery power source, and the driver circuit are disposed in the housing.

19. The ultrasound wave generating apparatus of claim 1, wherein the power source includes a battery power source, wherein the ultrasound wave generating apparatus includes a housing capable of being held in a hand, and wherein the battery power source, the driver circuit, and the ultrasound transducer are disposed in the housing.

20. The ultrasound wave generating apparatus of claim 1, wherein a current capacity of the driver circuit is at least 10 Amperes.

21. The ultrasound wave generating apparatus of claim 1, wherein a current capacity of the driver circuit is at least 50 Amperes.

22. The ultrasound wave generating apparatus of claim 1, wherein the driver circuit provides greater than 3 Amperes of current through the ultrasound transducer.

23. The ultrasound wave generating apparatus of claim 1, wherein the ultrasound transducer is capable of an impedance of less than 100 Ohms.

24. The ultrasound wave generating apparatus of claim 1, wherein the ultrasound transducer is capable of an impedance of less than 50 Ohms.

25. The ultrasound wave generating apparatus of claim 1, wherein the ultrasound transducer has an impedance of less than 15 Ohms when the driver circuit outputs the drive signal to drive the transducer at a frequency corresponding to the resonant frequency.

26. The ultrasound wave generating apparatus of claim 1, wherein the ultrasound transducer has an impedance in the range of between about 0.37 Ohms and about 15 Ohms when the driver circuit outputs the drive signal to drive the transducer at a frequency corresponding to the resonant frequency.

27. The ultrasound wave generating apparatus of claim 1, wherein the ultrasound transducer has an impedance in the range of between about 0.37 Ohms and about 5 Ohms when the driver circuit outputs the drive signal to drive the transducer at a frequency corresponding to the resonant frequency.

28. The ultrasound wave generating apparatus of claim 1, wherein the ultrasound transducer has an impedance of less than 2 Ohms when the driver circuit outputs the drive signal to drive the transducer at a frequency corresponding to the resonant frequency.

29. The ultrasound wave generating apparatus of claim 1, wherein the power source includes a battery power source, wherein the ultrasound wave generating apparatus includes a housing capable of being held in a hand, wherein the battery power source and the driver circuit are disposed in the housing, and wherein the transducer is capable of an impedance of less than 100 Ohms.

30. The ultrasound wave generating apparatus of claim 1, wherein the ultrasound transducer is a single element ultrasound transducer having a single transducer element.

31. The ultrasound wave generating apparatus of claim 1, wherein the ultrasound transducer is a multiple element ultrasound transducer having three or fewer transducer elements.

32. The ultrasound wave generating apparatus of claim 1, wherein the ultrasound transducer is a multiple element ultrasound transducer having a plurality of transducer elements arranged in layers.

33. The ultrasound wave generating apparatus of claim 1, wherein the driver circuit provides greater than 1 Ampere of current through the ultrasound transducer.

34. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is an imbalanced continuous bipolar drive signal so that both of compression forces and expansion forces are imparted to the ultrasound transducer, and further so that the compression forces are of greater magnitude than the expansion forces.

35. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the transistor based driver circuit includes a plurality of transistor pairs connected in parallel, each of the transistor pairs having first and second transistors, wherein each of the transistor pairs is coupled to the first and second clamping voltage terminals.

36. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;

wherein the ultrasound wave generating apparatus is adapted so that the ultrasound transducer is incorporated in a replaceable ultrasound transducer assembly that is one of a plurality of candidate ultrasound transducer assemblies that can be associated to the ultrasound wave generating apparatus, and wherein the ultrasound wave generating apparatus is operative so that the drive signal has at least one characteristic that is responsive to which of the plurality of candidate ultrasound transducer assemblies is presently associated to the ultrasound wave generating apparatus.

37. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the ultrasound wave generating apparatus includes a user interface and is adapted so that the ultrasound transducer is incorporated in a replaceable ultrasound transducer assembly that is one of a plurality of candidate ultrasound transducer assemblies that can be associated to the ultrasound wave generating apparatus, wherein the ultrasound wave generating apparatus is operative so that the drive signal output by the driver circuit is responsive to each of (a) a switching of a candidate transducer assembly, and (b) a control input that is input by an operator utilizing the user interface.

38. The ultrasound wave generating apparatus of claim 37, wherein each of the plurality of candidate transducer assemblies includes a timing device disposed therein for controlling a timing of the driver circuit.

39. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the ultrasound wave generating apparatus is operative in a first mode of operation and in a second mode of operation, wherein the ultrasound wave generating apparatus in the first mode of operation outputs an imbalanced bipolar output drive signal, wherein the apparatus in the second mode of operation outputs an output drive signal that is selected from the group consisting of a unipolar output drive signal and a balanced output drive signal.

40. The ultrasound wave generating apparatus of claim 39, wherein the ultrasound wave generating apparatus includes a replaceable transducer assembly incorporating the transducer, the transducer assembly being one of a plurality of candidate transducer assemblies, wherein the ultrasound wave generating apparatus is operative so that the ultrasound wave generating apparatus switches operation from the first mode of operation to the second mode of operation responsively to the transducer assembly being replaced with another of the plurality of candidate transducer assemblies.

41. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;

wherein the transducer comprises first and second transducer elements having different resonant frequencies so that the ultrasound transducer includes a plurality of resonant frequencies, the first transducer element having a first resonant frequency, the second transducer element having a second resonant frequency.

42. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the ultrasound transducer comprises first and second transducer elements having different resonant frequencies so that the ultrasound transducer includes a plurality of resonant frequencies, the first transducer element having a first resonant frequency, the second transducer element having a second resonant frequency, and wherein the apparatus is configured so that the driver circuit is operative to output a frequency sweeping drive signal, the frequency sweeping drive signal having a frequency corresponding to the first resonant frequency during a first period, the frequency sweeping drive signal having a frequency corresponding to the second resonant frequency during a second period.

43. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;
wherein the power supply has a plurality of power supply stages, each power supply stage having an associated driver circuit and power source, wherein the plurality of the power supply stages include first and second power supply stages, the second power supply stage being successive in relation to the first power supply stage, and wherein an output of the first of the power supply stages is input into a stage ground of the second power supply stage.

44. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the driver circuit is operative to output a drive signal having a frequency corresponding to the resonant frequency; and
wherein the apparatus is configured so that the transducer has an associated load voltage when the driver circuit outputs the drive signal to drive the transducer at a frequency corresponding to the resonant frequency, wherein the apparatus is further configured so that the driver circuit has an associated source voltage when the driver circuit outputs the drive signal at a frequency corresponding to the resonant frequency, and wherein the apparatus is configured so that the amplitude of the load voltage is at least 90 percent of the amplitude of the source voltage when the driver circuit outputs a drive signal at a frequency corresponding to the resonant frequency;

wherein the power supply includes a user interface configured to permit an operator to independently adjust the first terminal clamping voltage and the second terminal clamping voltage via input of control inputs utilizing the user interface.

45. An ultrasound wave generating apparatus comprising:
a power supply having a power source, a timing circuit, and a transistor based driver circuit for output of a drive signal, wherein the driver circuit includes first and second clamping voltage terminals, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the transistor based driver circuit includes a plurality of transistor pairs connected in parallel, each of the transistor pairs having first and second transistors, wherein each of the transistor pairs is coupled to the first and second clamping voltage terminals.

46. The ultrasound wave generating apparatus of claim 45, wherein the ultrasound wave generating apparatus includes a probe having a housing in which the ultrasound transducer is disposed, the probe housing receiving an ultrasound coupling medium.

47. The ultrasound wave generating apparatus of claim 45, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

48. The ultrasound wave generating apparatus of claim 45, wherein the plurality of transistor pairs connected in parallel include a transistor pair and a second transistor pair, wherein the second transistor pair is connected in parallel with the transistor pair.

49. The ultrasound wave generating apparatus of claim 45, wherein a transistor pair of the plurality of transistor pairs is a MOSFET transistor pair including a first transistor provided by an NMOS transistor and a second transistor provided by a PMOS transistor.

50. The ultrasound wave generating apparatus of claim 49, wherein the transistor pair of the plurality of transistor pairs is operative to alternate between conditions of (a) the NMOS transistor cut off, with the PMOS transistor conducting and (b) the PMOS transistor cut off, with the NMOS transistor conducting.

51. The ultrasound wave generating apparatus of claim 45, wherein each transistor pair of the plurality of transistor pairs is a MOSFET transistor pair including a first transistor provided by an NMOS transistor and a second transistor provided by a PMOS transistor.

52. The ultrasound wave generating apparatus of claim 45, wherein each transistor pair of the plurality of transistor pairs is a MOSFET transistor pair including a first transistor provided by an NMOS transistor having a source coupled to the first clamping voltage terminal and a second transistor provided by a PMOS transistor having a source coupled to the second clamping voltage terminal.

53. The ultrasound wave generating apparatus of claim 45, wherein a transistor pair of the plurality of transistor pairs is a MOSFET transistor pair including a first transistor provided by an NMOS transistor and a second transistor provided by a PMOS transistor, wherein an input of the transistor pair is commonly connected to respective gates of the first transistor and the second transistor of the transistor pair, and wherein respective drains of the first transistor and the second transistor of the transistor pair are commonly connected to an output of the transistor pair for driving the ultrasound transducer.

54. The ultrasound wave generating apparatus of claim 45, wherein a transistor pair of the plurality of transistor pairs is a MOSFET transistor pair including a first transistor provided by an NMOS transistor and a second transistor provided by a PMOS transistor, wherein an input of the transistor pair is commonly connected to respective gates of the first transistor and the second transistor of the transistor pair, and wherein respective drains of the first transistor and the second transistor of the transistor pair are commonly connected to an output of the transistor pair for driving the ultrasound transducer, wherein a second transistor pair of the plurality of transistor pairs is a MOSFET transistor pair including a first transistor provided by an NMOS transistor and a second transistor provided by a PMOS transistor, wherein the input of the transistor pair is commonly connected to respective gates of the first transistor and the second transistor of the second transistor pair, and wherein respective drains of the first transistor and the second transistor of the second transistor pair are commonly connected to the output of the transistor pair for driving the ultrasound transducer.

55. The ultrasound wave generating apparatus of claim 45, wherein the driver circuit provides greater than 1 Ampere of current through the ultrasound transducer.

56. The ultrasound wave generating apparatus of claim 45, wherein a current capacity of the driver circuit is at least 10 Amperes.

57. The ultrasound wave generating apparatus of claim 45, wherein the ultrasound transducer is capable of an impedance of less than 100 Ohms.

58. The ultrasound wave generating apparatus of claim 45, wherein the ultrasound transducer is capable of an impedance of less than 50 Ohms.

59. The ultrasound wave generating apparatus of claim 45, wherein the ultrasound transducer has an impedance of less than 15 Ohms when the driver circuit outputs the drive signal to drive the transducer at a frequency corresponding to the resonant frequency.

60. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;

an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;

wherein the ultrasound transducer is operative so that compression force is imparted to the ultrasound transducer when the drive signal is of a first voltage polarity, and further so that an expansion force is imparted to the ultrasound transducer when the drive signal is of a second voltage polarity, and further so that the drive signal is an imbalanced continuous bipolar drive signal so that both of compression forces and expansion forces are imparted to the ultrasound transducer, and further so that the compression forces are of greater magnitude than the expansion forces.

61. The ultrasound wave generating apparatus of claim 60, wherein the ultrasound wave generating apparatus includes a probe having a housing in which the ultrasound transducer is disposed, the probe housing receiving an ultrasound coupling medium.

62. The ultrasound wave generating apparatus of claim 60, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

63. The ultrasound wave generating apparatus of claim 60, wherein the power source includes a battery power source, wherein the ultrasound wave generating apparatus includes a housing capable of being held in a hand, and wherein the battery power source, and the driver circuit are disposed in the housing.

64. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer; and
wherein the ultrasound wave generating apparatus is adapted so that the ultrasound transducer is incorporated in a replaceable ultrasound transducer assembly that is one of a plurality of candidate ultrasound transducer assemblies that can be associated to the ultrasound wave generating apparatus, and wherein the ultrasound wave generating apparatus is operative so that the drive signal has at least one characteristic that is responsive to which of the plurality of candidate ultrasound transducer assemblies is presently associated to the ultrasound wave generating apparatus.

65. The ultrasound wave generating apparatus of claim 64, wherein the ultrasound wave generating apparatus is operative in a first mode of operation and in a second mode of operation, wherein the ultrasound wave generating apparatus in the first mode of operation outputs an imbalanced bipolar output drive signal, wherein the apparatus in the second mode of operation outputs an output drive signal that is selected from the group consisting of a unipolar output drive signal and a balanced output drive signal, wherein the ultrasound wave generating apparatus includes a replaceable transducer assembly incorporating the transducer, the transducer assembly being one of a plurality of candidate transducer assemblies, wherein the ultrasound wave generating apparatus is operative so that the ultrasound wave generating apparatus switches operation from the first mode of operation to the second mode of operation responsively to the transducer assembly being replaced with another of the plurality of candidate transducer assemblies.

66. The ultrasound wave generating apparatus of claim 64, wherein the ultrasound wave generating apparatus includes a probe having a housing in which the ultrasound transducer is disposed, the probe housing receiving an ultrasound coupling medium.

67. The ultrasound wave generating apparatus of claim 64, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

68. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the ultrasound transducer comprises first and second transducer elements having different resonant frequencies so that the ultrasound transducer includes a plurality of resonant frequencies, the first transducer element having a first resonant frequency, the second transducer element having a second resonant frequency.

69. The ultrasound wave generating apparatus of claim 68, wherein the apparatus is configured so that the driver circuit is operative to output a frequency sweeping drive signal, the frequency sweeping drive signal having a frequency corresponding to the first resonant frequency during a first period, the frequency sweeping drive signal having a frequency corresponding to the second resonant frequency during a second period.

70. The ultrasound wave generating apparatus of claim 68, wherein the ultrasound wave generating apparatus includes a probe having a housing in which the ultrasound transducer is disposed, the probe housing receiving an ultrasound coupling medium.

71. The ultrasound wave generating apparatus of claim 68, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

72. An ultrasound wave generating apparatus comprising:
a power supply having a power source, a timing circuit, and a transistor based driver circuit for output of a drive signal, wherein the driver circuit includes a transistor pair including first and second transistors, and first and second clamping voltage terminals, the first and second transistors having respective first and second gates, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the power supply includes a user interface configured to permit an operator to independently adjust the first terminal clamping voltage and the second terminal clamping voltage via input of control inputs utilizing the user interface.

73. The ultrasound wave generating apparatus of claim 72, wherein the ultrasound wave generating apparatus includes a probe having a housing in which the ultrasound transducer is disposed, the probe housing receiving an ultrasound coupling medium.

74. The ultrasound wave generating apparatus of claim 72, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

75. An ultrasound wave generating apparatus comprising:
a power supply having a power source, a timing circuit, and a transistor based driver circuit for output of a drive signal, wherein the driver circuit includes first and second clamping voltage terminals, wherein the timing circuit is operative to output a timing signal for controlling timing of the drive signal output by the driver circuit;
an ultrasound transducer configured to emit ultrasound energy, the ultrasound transducer being coupled to the driver circuit so that the drive signal output by the driver circuit drives the ultrasound transducer, wherein a frequency at which the ultrasound transducer emits maximum power when driven by the output drive signal defines a resonant frequency of the ultrasound transducer;
wherein the transistor based driver circuit includes a transistor pair having a first transistor and a second transistor, wherein an input of the transistor pair is commonly connected to respective gates of the first transistor and the second transistor of the transistor pair, and wherein respective drains of the first transistor and the second transistor of the transistor pair are commonly connected to an output of the transistor pair for driving the ultrasound transducer.

76. The ultrasound wave generating apparatus of claim 75, wherein the transistor based driver circuit includes a plurality of transistor pairs, the plurality of transistor pairs including the transistor pair and a second transistor pair, wherein the second transistor pair of the plurality of transistor pairs is a MOSFET transistor pair including a first transistor provided by an NMOS transistor and a second transistor provided by a PMOS transistor, wherein the input of the transistor pair is commonly connected to respective gates of the first transistor and the second transistor of the second transistor pair, and wherein respective drains of the first transistor and the second transistor of the second transistor pair are commonly connected to the output of the transistor pair for driving the ultrasound transducer.

77. The ultrasound wave generating apparatus of claim 75, wherein the ultrasound wave generating apparatus includes a probe having a housing in which the ultrasound transducer is disposed, the probe housing receiving an ultrasound coupling medium.

78. The ultrasound wave generating apparatus of claim 75, wherein the power source includes a battery power source, wherein the ultrasound wave generating apparatus includes a portable housing and a probe housing, wherein the battery power source is disposed in the portable housing, wherein the ultrasound transducer is disposed in the probe housing, and wherein a transmission line is disposed between the portable housing and the probe housing.

* * * * *